United States Patent
Komine et al.

(10) Patent No.: US 11,445,957 B2
(45) Date of Patent: Sep. 20, 2022

(54) PHYSIOLOGICAL-CONDITION ASSESSING DEVICE, PHYSIOLOGICAL-CONDITION ASSESSING METHOD, PROGRAM FOR PHYSIOLOGICAL-CONDITION ASSESSING DEVICE, AND PHYSIOLOGICAL-CONDITION ASSESSING SYSTEM

(71) Applicant: NATIONAL INSTITUTE OF ADVANCED INDUSTRIAL SCIENCE AND TECHNOLOGY, Tokyo (JP)

(72) Inventors: Hidehiko Komine, Tsukuba (JP); Satoshi Kitazaki, Tsukuba (JP); Motoyuki Akamatsu, Tsukuba (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 947 days.

(21) Appl. No.: 16/310,717

(22) PCT Filed: Jul. 5, 2017

(86) PCT No.: PCT/JP2017/024585
§ 371 (c)(1),
(2) Date: Dec. 17, 2018

(87) PCT Pub. No.: WO2018/008666
PCT Pub. Date: Jan. 11, 2018

(65) Prior Publication Data
US 2020/0315512 A1 Oct. 8, 2020

(30) Foreign Application Priority Data
Jul. 7, 2016 (JP) .............................. JP2016-135512

(51) Int. Cl.
*A61B 5/18* (2006.01)
*G16H 40/67* (2018.01)
(Continued)

(52) U.S. Cl.
CPC ............... *A61B 5/18* (2013.01); *G16H 10/60* (2018.01); *G16H 20/10* (2018.01); *G16H 40/67* (2018.01);
(Continued)

(58) Field of Classification Search
CPC ....... A61B 5/18; A61B 5/0059; A61B 5/0077; A61B 5/01; A61B 5/053; A61B 5/1112;
(Continued)

(56) References Cited

U.S. PATENT DOCUMENTS 6,575,902 B1 * 6/2003 Burton ................... G08B 21/06
600/595
10,210,678 B1 * 2/2019 Manzella ............... G07C 5/008
(Continued)

FOREIGN PATENT DOCUMENTS

JP 2005087486 A 4/2005
JP 2007122579 A 5/2007
(Continued)

OTHER PUBLICATIONS

International Search Report dated Aug. 22, 2017 for PCT/JP2017/024585 and English translation.

*Primary Examiner* — Ryan W Sherwin
(74) *Attorney, Agent, or Firm* — Lucas & Mercanti, LLP

(57) ABSTRACT

A physiological condition assessing method includes: acquiring a driving-time physiological data measured when a subject is driving a vehicle; acquiring a driving-characteristic data indicating driving characteristics; acquiring a period driving-time physiological data, a period driving-characteristic data and period non-driving-time physiologi-
(Continued)

cal data corresponding to a first period including the measurement time point of the driving-time physiological data and the measurement time point of the driving-characteristic data, and a second period having a different length to the first period; generating a driving-time physiological feature from the driving-time physiological data and the period driving-time physiological data; generating a driving-characteristic feature; generating a non-driving-time physiological feature quantity; and assessing a physiological condition of the subject, from the non-driving-time physiological feature and at least one of the driving-time physiological feature and the driving-characteristic feature.

15 Claims, 20 Drawing Sheets

(51) Int. Cl.
| | | |
|---|---|---|
| *G16H 50/50* | (2018.01) | |
| *G16H 10/60* | (2018.01) | |
| *G16H 50/30* | (2018.01) | |
| *G16H 50/70* | (2018.01) | |
| *G16H 50/20* | (2018.01) | |
| *G16H 20/10* | (2018.01) | |
| *A61B 5/00* | (2006.01) | |
| *A61B 5/01* | (2006.01) | |
| *A61B 5/053* | (2021.01) | |
| *A61B 5/11* | (2006.01) | |
| *A61B 8/00* | (2006.01) | |

(52) U.S. Cl.
CPC ............ *G16H 50/20* (2018.01); *G16H 50/30* (2018.01); *G16H 50/50* (2018.01); *G16H 50/70* (2018.01); *A61B 5/0059* (2013.01); *A61B 5/0077* (2013.01); *A61B 5/01* (2013.01); *A61B 5/053* (2013.01); *A61B 5/1112* (2013.01); *A61B 8/00* (2013.01); *A61B 2560/0257* (2013.01); *A61B 2562/0204* (2013.01); *A61B 2562/0219* (2013.01); *A61B 2562/0223* (2013.01); *A61B 2562/0247* (2013.01)

(58) Field of Classification Search
CPC .............. A61B 8/00; A61B 2560/0257; A61B 2562/0204; A61B 2562/0219; A61B 2562/0223; A61B 2562/0247; A61B 5/11; A61B 5/00; G16H 10/60; G16H 20/10; G16H 40/67; G16H 50/20; G16H 50/30; G16H 50/50; G16H 50/70; B60W 2040/0872; B60W 40/09
See application file for complete search history.

(56) References Cited

U.S. PATENT DOCUMENTS

| | | | |
|---|---|---|---|
| 10,223,751 B1* | 3/2019 | Hutchinson | G06F 16/2365 |
| 10,610,145 B2* | 4/2020 | Sham | A61B 5/318 |
| 2003/0181822 A1* | 9/2003 | Victor | A61B 5/1114 |
| | | | 600/558 |
| 2010/0007480 A1* | 1/2010 | Uozumi | B60Q 9/00 |
| | | | 340/576 |
| 2012/0154156 A1* | 6/2012 | Kuntzel | G08B 21/06 |
| | | | 340/575 |
| 2013/0253841 A1* | 9/2013 | Matsunaga | A61B 5/6893 |
| | | | 702/19 |
| 2014/0240132 A1* | 8/2014 | Bychkov | A61B 5/18 |
| | | | 340/576 |
| 2015/0246673 A1* | 9/2015 | Tseng | B60W 30/12 |
| | | | 701/23 |
| 2016/0086393 A1* | 3/2016 | Collins | A61B 5/024 |
| | | | 701/31.5 |
| 2016/0133117 A1* | 5/2016 | Geller | A61B 5/746 |
| | | | 340/457 |
| 2017/0011562 A1* | 1/2017 | Hodges | H04W 4/46 |
| 2017/0144671 A1* | 5/2017 | Memani | B60W 40/09 |
| 2017/0166217 A1* | 6/2017 | Sbianchi | H04B 1/1036 |
| 2017/0324752 A1* | 11/2017 | Todasco | H04L 63/0853 |
| 2018/0025656 A1* | 1/2018 | Cronin | G09B 5/06 |
| | | | 434/236 |
| 2021/0153796 A1* | 5/2021 | De Weser | A61B 5/0205 |
| 2022/0180750 A1* | 6/2022 | Chen | G08G 1/163 |

FOREIGN PATENT DOCUMENTS

| | | |
|---|---|---|
| JP | 2008183205 A | 8/2008 |
| JP | 2015203994 A | 11/2015 |
| WO | 2014017090 A1 | 1/2014 |

* cited by examiner

PHYSIOLOGICAL-CONDITION ASSESSING DEVICE, PHYSIOLOGICAL-CONDITION ASSESSING METHOD, PROGRAM FOR PHYSIOLOGICAL-CONDITION ASSESSING DEVICE, AND PHYSIOLOGICAL-CONDITION ASSESSING SYSTEM

CROSS REFERENCE TO RELATED APPLICATION

This Application is a 371 of PCT/JP2017/024585 filed on Jul. 5, 2017 which, in turn, claimed the priority of Japanese Patent Application No. 2016-135512 filed on Jul. 7, 2016, both applications are incorporated herein by reference.

TECHNICAL FIELD

The present invention relates to techniques for a physiological-condition assessing device for assessing a physiological condition of a subject, a physiological-condition assessing method, a program for the physiological-condition assessing device, and a physiological-condition assessing system.

BACKGROUND ART

A system for conducting health management has been developed by measuring the human body with various sensors. For example, Patent Literature 1 discloses a physical condition management system for detecting exercise-time biological information during exercise, detecting bed-time biological information while going to bed, computing bedtime physical condition information based on the exercise-time biological information and the bedtime biological information, and assisting sleep onset based on the bedtime physical condition information.

CITATION LIST

Patent Literature

Patent Literature 1: JP 2008-183205 A

SUMMARY OF INVENTION

Problem to be Solved by the Invention

However, in the prior art like Patent Literature 1, though the physical condition that changes constantly every moment is monitored in real time, for example, it was not possible to capture the sign of disease and the like more quickly. In addition, in the prior art, it was not possible to cope with various diseases and symptoms.

Hence, it is an object of the present invention to provide, for example, a physiological-condition assessing device that captures signs of illness more quickly, for various diseases and symptoms.

Means for Solving the Problem

To solve the above problem, the invention according to claim 1 includes: driving-time physiological data acquiring means for acquiring a driving-time physiological data of a subject measured when the subject is driving a vehicle, and a measurement time point of the driving-time physiological data; driving-characteristic data acquiring means for acquiring a driving-characteristic data indicating a driving characteristic in which the subject drives the vehicle, and a measurement time point of the driving-characteristic data; period driving-time physiological data acquiring means for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means for storing the driving-time physiological data measured in the past; period driving-characteristic data acquiring means for acquiring a period driving-characteristic data corresponding to the first period and the second period, with reference to a second storage means for storing the driving-characteristic data measured in the past; period non-driving-time physiological data acquiring means for acquiring a period non-driving-time physiological data corresponding to at least one of the first period and the second period, with reference to a third storage means for storing a non-driving-time physiological data measured in the past that is the physiological data of the subject when the subject is not driving the vehicle; driving-time physiological feature generating means for generating a driving-time physiological feature indicating feature of the physiological data of the subject while driving, from the driving-time physiological data and the period driving-time physiological data; driving-characteristic feature generating means for generating a driving-characteristic feature indicating feature of the driving characteristic of the subject while driving, from the driving-characteristic data and the period driving-characteristic data; non-driving-time physiological feature generating means for generating a non-driving-time physiological feature indicating feature of the physiological data of the subject while not driving, from the period non-driving-time physiological data; and physiological-condition assessing means for assessing a physiological condition of the subject, from the non-driving-time physiological feature and at least one of the driving-time physiological feature and the driving-characteristic feature.

The invention according to claim 2 is the physiological-condition assessing device according to claim 1 in which the physiological-condition assessing means assesses the physiological condition of the subject in a feature space of feature vectors composed of the non-driving-time physiological feature and at least one of the driving-time physiological feature and the driving-characteristic feature.

The invention according to claim 3 is the physiological-condition assessing device according to any one of claim 1 or 2, further including feature selecting means for selecting a feature used in the physiological condition, for each physiological condition among a plurality of physiological conditions to be assessed, from a plurality of the driving-time physiological features, a plurality of the driving-characteristic features, and a plurality of the non-driving-time physiological features.

The invention according to claim 4 is the physiological-condition assessing device according to any one of claims 1 to 3, in which the driving-time physiological feature generating means generates amount of change over time of the driving-time physiological data as the driving-time physiological feature, from the driving-time physiological data with reference to the first storage means, based on age of the subject calculated from subject information including birth time of the subject, the driving-characteristic feature generating means generates amount of change over time of the driving-characteristic data as the driving-characteristic feature, with reference to the second storage means, based on the age of the subject, and the non-driving-time physiological feature generating means generates amount of change over time of the non-driving-time physiological data as the non-driving-time physiological feature, from the non-driving-time physiological data with reference to the third storage means, based on the age of the subject.

The invention according to claim 5 is the physiological-condition assessing device according to claim 4, in which the amount of change over time is at least one of a slope of the change over time and a degree of difference from a baseline of the change over time.

The invention according to claim 6 is the physiological-condition assessing device according to any one of claims 1 to 5, further including driving-time/non-driving-time physiological feature generating means for generating a driving-time/non-driving-time physiological feature indicating feature of the physiological data of the subject while driving, based on difference between the driving-time physiological date and the period non-driving-time physiological data corresponding to at least one of the first period and the second period.

The invention according to claim 7 is the physiological-condition assessing device according to any one of claims 1 to 6, in which the first period or the second period is a season.

The invention according to claim 8 is the physiological-condition assessing device according to any one of claims 1 to 7, in which the first period or the second period is a driving day including the measurement time point of the driving-time physiological data or the measurement time point of the driving-characteristic data.

The invention according to claim 9 is the physiological-condition assessing device according to any one of claims 1 to 8 further including medication-physiological data acquiring means for acquiring a medication data on medication of the subject, from a terminal device which measures the medication data, in which the physiological-condition assessing means assesses the physiological condition of the subject, depending on a medication condition of the medication data.

The invention according to claim 10 is the physiological-condition assessing device according to any one of claims 1 to 9, further including driving-environment information acquiring means for acquiring driving-environment information of the vehicle, from position information of the vehicle when measuring the driving-time physiological data, in which the physiological-condition assessing means assesses the physiological condition of the subject, depending on the driving-environment information of the vehicle.

The invention according to claim 11 is the physiological-condition assessing device according to any one of claims 1 to 10, further including meteorological data acquiring means for acquiring a meteorological data when measuring the driving-time physiological data, from the measurement time point of the driving-time physiological data and position information of the vehicle when measuring the driving-time physiological data, in which the physiological-condition assessing means assesses the physiological condition of the subject, depending on a meteorological state of the meteorological data.

The invention according to claim 12 is the physiological-condition assessing device according to any one of claims 1 to 11, in which the period driving-time physiological data acquiring means that acquires the period driving-time physiological data of another subject corresponding to the first period and the second period, with reference to a fourth storage means for storing the driving-time physiological data of the other subject measured in the past, and the driving-time physiological feature generating means generates the driving-time physiological feature, from the driving-time physiological data and the period driving-time physiological data of the other subject.

The invention according to claim 13 includes: a step in which driving-time physiological data acquiring means stores acquires a driving-time physiological data of a subject measured when the subject is driving a vehicle, and a measurement time point of the driving-time physiological data; a step in which driving-characteristic data acquiring means acquires a driving-characteristic data indicating a driving characteristic in which the subject drives the vehicle, and a measurement time point of the driving-characteristic data; a step in which period driving-time physiological data acquiring means acquires a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means for storing the driving-time physiological data measured in the past; a step in which period driving-characteristic data acquiring means acquires a period driving-characteristic data corresponding to the first period and the second period, with reference to a second storage means for storing the driving-characteristic data measured in the past; a step in which period non-driving-time physiological data acquiring means acquires a period non-driving-time physiological data corresponding to at least one of the first period and the second period, with reference to a third storage means for storing a non-driving-time physiological data measured in the past that is the physiological data of the subject when the subject is not driving the vehicle; a step in which driving-time physiological feature generating means generates a driving-time physiological feature indicating feature of the physiological data of the subject while driving, from the driving-time physiological data and the period driving-time physiological data; a step in which driving-characteristic feature generating means generates a driving-characteristic feature indicating feature of the driving characteristic of the subject while driving, from the driving-characteristic data and the period driving-characteristic data; a step in which non-driving-time physiological feature generating means generates a non-driving-time physiological feature indicating feature of the physiological data of the subject while not driving, from the period non-driving-time physiological data; and a step in which physiological-condition assessing means assesses a physiological condition of the subject, from the non-driving-time physiological feature and at least one of the driving-time physiological feature and the driving-characteristic feature.

The invention according to claim 14 causes a computer to function as: driving-time physiological data acquiring means for acquiring a driving-time physiological data of a subject measured when the subject is driving a vehicle, and a measurement time point of the driving-time physiological data; driving-characteristic data acquiring means for acquiring a driving-characteristic data indicating a driving characteristic in which the subject drives the vehicle, and a measurement time point of the driving-characteristic data; period driving-time physiological data acquiring means for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means for storing the driving-time physiological data measured in the past; period driving-characteristic data acquiring means for acquiring a period driving-characteristic data corresponding to the first period and the second period, with reference to a second storage means for storing the driving-characteristic data measured in the past; period non-driving-time physiological data acquiring means for acquiring a period non-driving-time physiological data corresponding to at least one of the first period and the second period, with reference to a third storage means for storing a non-driving-time physiological data measured in the past that is the physiological data of the subject when the subject is not driving the vehicle; driving-time physiological feature generating means for generating a driving-time physiological feature indicating feature of the physiological data of the subject while driving, from the driving-time physiological data and the period driving-time physiological data; driving-characteristic feature generating means for generating a driving-characteristic feature indicating feature of the driving characteristic of the subject while driving, from the driving-characteristic data and the period driving-characteristic data; non-driving-time physiological feature generating means for generating a non-driving-time physiological feature indicating feature of the physiological data of the subject while not driving, from the period non-driving-time physiological data; and physiological-condition assessing means for assessing a physiological condition of the subject, from the non-driving-time physiological feature and at least one of the driving-time physiological feature and the driving-characteristic feature.

The invention according to claim 15 is a physiological-condition assessing system having: a physiological-condition assessing device for assessing a physiological condition of a subject; a mobile terminal device carried by the subject; and an in-vehicle terminal device installed in a vehicle that the subject drives, and the physiological-condition assessing device has: driving-time physiological data acquiring means for acquiring a driving-time physiological data of the subject measured when the subject is driving the vehicle, and a measurement time point of the driving-time physiological data; driving-characteristic data acquiring means for acquiring a driving-characteristic data indicating a driving characteristic in which the subject drives the vehicle, and a measurement time point of the driving-characteristic data; period driving-time physiological data acquiring means for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means for storing the driving-time physiological data measured in the past; period driving-characteristic data acquiring means for acquiring a period driving-characteristic data corresponding to the first period and the second period, with reference to a second storage means for storing the driving-characteristic data measured in the past; period non-driving-time physiological data acquiring means for acquiring a period non-driving-time physiological data corresponding to at least one of the first period and the second period, with reference to a third storage means for storing a non-driving-time physiological data measured in the past that is the physiological data of the subject when the subject is not driving the vehicle; driving-time physiological feature generating means for generating a driving-time physiological feature indicating feature of the physiological data of the subject while driving, from the driving-time physiological data and the period driving-time physiological data; driving-characteristic feature generating means for generating a driving-characteristic feature indicating feature of the driving characteristic of the subject while driving, from the driving-characteristic data and the period driving-characteristic data; non-driving-time physiological feature generating means for generating a non-driving-time physiological feature indicating feature of the physiological data of the subject while not driving, from the period non-driving-time physiological data; and physiological-condition assessing means for assessing the physiological condition of the subject, from the non-driving-time physiological feature and at least one of the driving-time physiological feature and the driving-characteristic feature.

Effect of the Invention

Considering the influence of human biorhythm and external environment for driving-time physiological data and driving-characteristics data in a state where predetermined physical and mental load amount exist while driving in which a change in physiological condition appears easily, the present invention assesses physiological condition from driving-time physiological data, non-driving-time physiological data, and driving-characteristic data corresponding to a plurality of periods such as a first period and a second period having a different length to the first period. Accordingly, since the present invention generates quantified features and uses the various features from the physiological data, the driving-characteristic data different from the physiological data, and data according to the difference in the load on the subject such as driving or non-driving, it is possible to evaluate or analyze the physiological condition more accurately and quantitatively. Furthermore, it is possible to capture signs of changes in various physiological conditions.

DESCRIPTION OF EMBODIMENTS

The following describes an embodiment of the present invention with reference to the drawings. In the embodiment described below, the present invention is applied to a physiological-condition assessing system.

[1. Configuration and Functional Overview of Physiological-Condition Assessing System]

Figure 1:
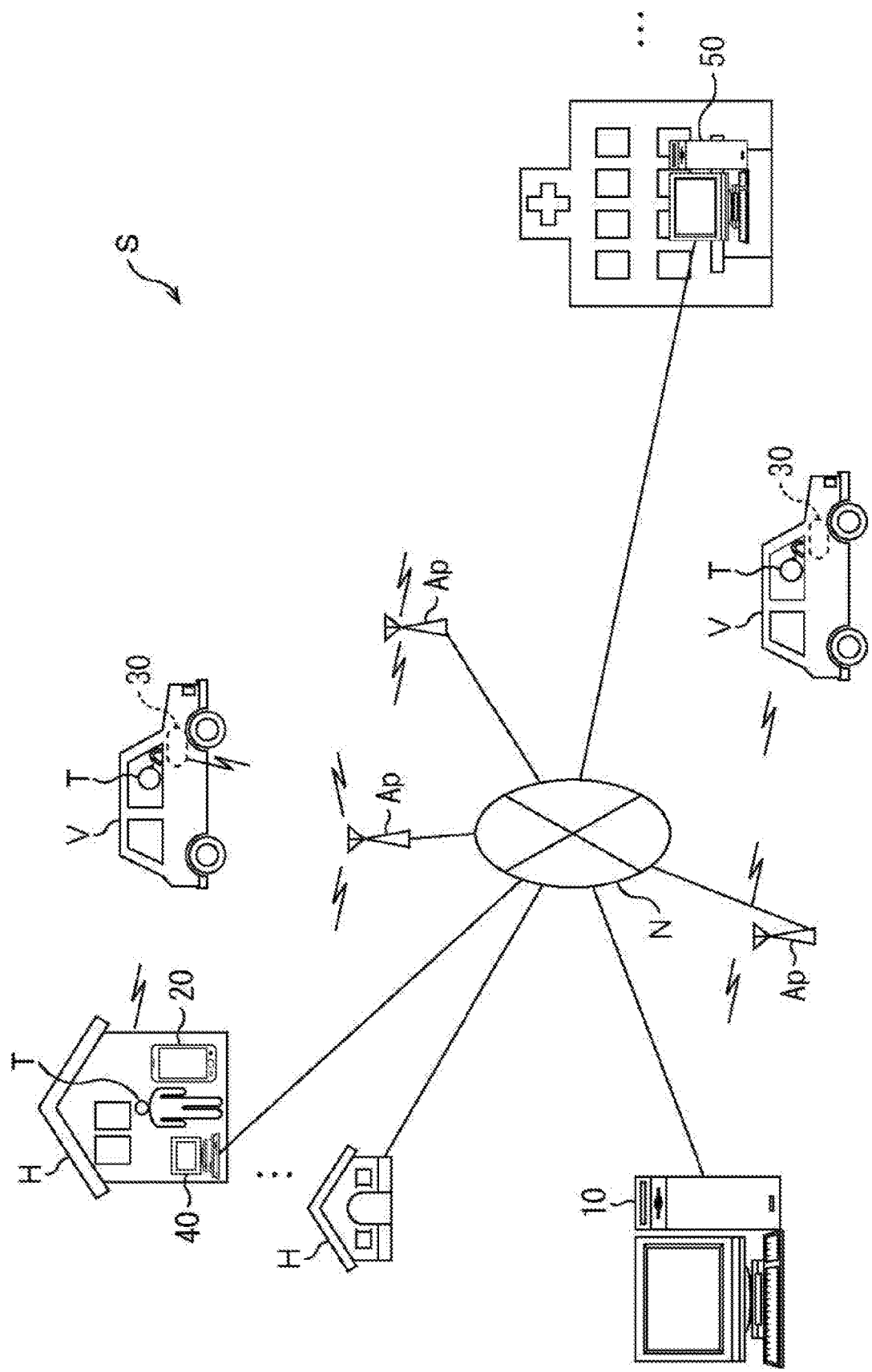
FIG. 1 is a schematic diagram schematically showing an example configuration of a physiological-condition assessing system according to an embodiment.

First, a configuration of a physiological-condition assessing according to an embodiment of the present invention is described using FIG. 1. FIG. 1 is a schematic diagram schematically showing an example configuration of a physiological-condition assessing system S according to an embodiment.

As shown in FIG. 1, the physiological-condition assessing system S includes a physiological-condition assessing server device 10 (an example of a physiological-condition assessing device), mobile terminal devices 20, in-vehicle terminal devices 30, home terminal devices 40, and a medical institution server device 50. The physiological-condition assessing server device 10 acquires, for example, physiological data of each of subjects T and assesses physiological condition of the subjects T. Each mobile terminal device 20 is carried by the subject T and transmits the physiological data of subject T to the physiological-condition assessing server device 10. Each in-vehicle terminal device 30 collects, for example, physiological data when the subject T is at a home H. The medical institution server device 50 is of a medical institution used by subjects T.

The physiological-condition assessing server device 10 is capable of exchanging data with each mobile terminal device 20, each in-vehicle terminal device 30, each home terminal device 40, and the medical institution server device 50 over a network N using communication protocols, such as TCP/IP. The network N includes, for example, the Internet.

In the network, meteorological server devices (not shown) and driving environment provision server devices (not shown) are connected. The meteorological server devices provide meteorological data to the physiological-condition assessing server device 10. The driving environment provision server devices provide road information (an example of driving environment information) such as information on traffic congestion, temporary stop place, one way road, two lane road, and road with median strip. Herein, an example of the driving environment information includes, for example, whether it is a highway or a general road, whether the width of the road is narrow or wide, whether it is an always used road or a road used for the first time, whether there are many or few pedestrians, whether vehicle traffic volume is high or low (even if it cannot say that it is congestion). In addition, an example of driving environment information includes, for example, information that the sunshine is dazzling depending on the time zone, roads where drivers are nervous easily, roads where heart rate tends to rise, length of driving time, probability of occurrence of accidents by each location. The information on traffic congestion may include information on whether traffic was congested, time zone such as rush hour, infrastructure information such as road construction and accident.

Incidentally, the network N may include, for example, a dedicated communication line, a mobile communication network, and a gateway. The network N may include access points Ap. For example, the mobile terminal device 20 and the in-vehicle terminal device 30 may be connectable to the network N through the access point Ap.

The physiological-condition assessing server device 10 has a function of a computer. The physiological-condition assessing server device 10 acquires physiological data of the subjects T from each mobile terminal device 20. The physiological-condition assessing server device 10 acquires data of each vehicle V which each in-vehicle terminal device 30 collected. The physiological-condition assessing server device 10 acquires meteorological data from the meteorological server devices. The physiological-condition assessing server device 10 acquires driving environment information from the driving environment provision server devices.

Each mobile terminal device 20 has a function of a computer. The mobile terminal device 20 is, for example, a smartphone or a tablet terminal. The mobile terminal device 20 collects physiological data from sensors which measure physiological data of the subject T.

Each in-vehicle terminal device 30 has a function of a computer. The in-vehicle terminal device 30 is, for example, a navigation device of the vehicle V. The mobile terminal device 20 and the in-vehicle terminal device 30 can communicate by wireless communication. The in-vehicle terminal device 30 is installed in the vehicle V which the subject T drives. The vehicle V is, for example, a vehicle owned by the subject T himself/herself, family, acquaintance or the company, or a vehicle rented.

Each home terminal device 40 has a function of a computer. The home terminal device 40 is installed in, for example, the home H of the subject T or his/her workplace. The home terminal device 40 is, for example, a personal computer. The mobile terminal device 20 and the home terminal device 40 can communicate by wireless communication.

The medical institution server device 50 has a function of a computer. The medical institution server device 50 is installed in, for example, medical institutions such as hospitals and core center of regional medicine. The medical institution server device 50 has electronic medical records information which record information, such as result of consultation, examination order, and results of examination on the subject T.

Herein, an example of physiological condition includes signs of sick, disease developing risk, symptom developing risk, and signs of change in physical condition. An example of physical condition may include levels of physical condition. For example, regarding physical condition, it may be "health" and "poor physical condition," or it is divided into levels, such as "good, somewhat good, somewhat abnormal, abnormal", etc. In case of indicating the level of physical condition, disease name and the like may not be specified. Risks and levels are an example of quantitative assessment.

Examples of diseases include cardiovascular disease such as myocardial infarction, stroke, hypertonia and arrhythmia, sleep apnea syndrome, dementia, declining consciousness level due to diabetes, and epileptic seizure. Examples of symptoms include palpitations, shortness of breath, constipation, fever, chills, diarrhea, numbness, pain.

With regard to the determination of the sign of the symptom, it may be determined by a single index or a combination of indices. For example, palpitations may be determined only by heart rate, and shortness of breath may be uniquely determined by respiration rate (measured by thoracic movement, etc.). Moreover, blood pressure may be added to determine "effect due to shortness of breath".

An example of physiological condition may include levels of condition of each viscera or organ and levels of condition of each biological function (for example, digestive function, cardiovascular function, function of the nervous system, metabolic function and cognitive function, etc.). These levels may be levels corresponding to the specific numerical value such as blood test, considering age of the subject T and body weight, etc.

An example of physiological condition may include probability of occurrence of a predetermined illness (developing risk). Instead of value of the probability, the predetermined illness may be "sick A is less likely to develop", "sick A is apt to develop somewhat", "sick A is likely to develop", "sick A has become apparent", etc.

An example of physiological condition may include multiple sick, for example, "sick A and sick B are likely to develop", etc.

An example of physiological condition may include "the risk of developing sick A exceeded the first threshold", "the risk of developing sick B exceeded the first threshold", . . . , "the risk of developing sick A exceeded nth threshold", and "the risk of developing sick B exceeded nth threshold".

As levels of physiological condition, it may be based on a combination of a number exceeding the threshold value or sick exceeding the threshold value for each sick.

In addition, examples of levels of physiological condition may include that value of the predetermined physiological data (or, driving-characteristic data of each subject T who is driving the vehicle V) "exceeded the first threshold", . . . , "exceeded the nth threshold". The level of the physiological condition may be based on a combination of multiple data.

In addition, not only captured in each individual physiological condition, but each of physiological conditions may be handled concurrently in a vector space (feature space of feature vectors). An index of each physiological condition may be captured in an n-dimensional vector space and may be handled like the level of the physiological condition by the positional relationship in the vector space.

[2. Configuration and Functions of Information Processing Server and Each Terminal Device]

(2.1 Configuration and Functions of Physiological-Condition Assessing Server Device 10)

The following describes a configuration and functions of the physiological-condition assessing server device 10 using FIGS. 2 to 9.

Figure 2:
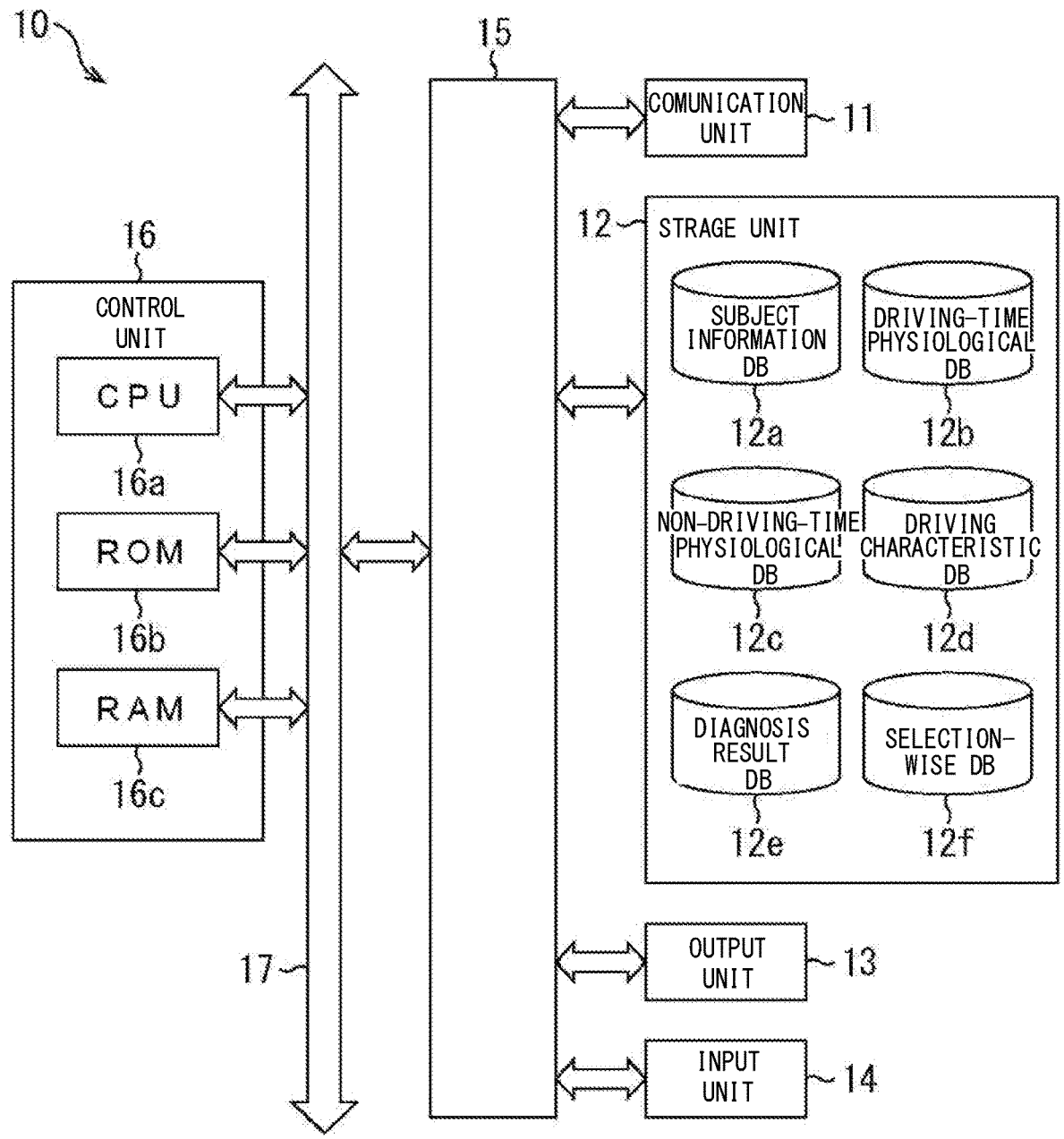
FIG. 2 is a block diagram schematically showing an example configuration of an information processing server device in FIG. 1.
Figure 3:
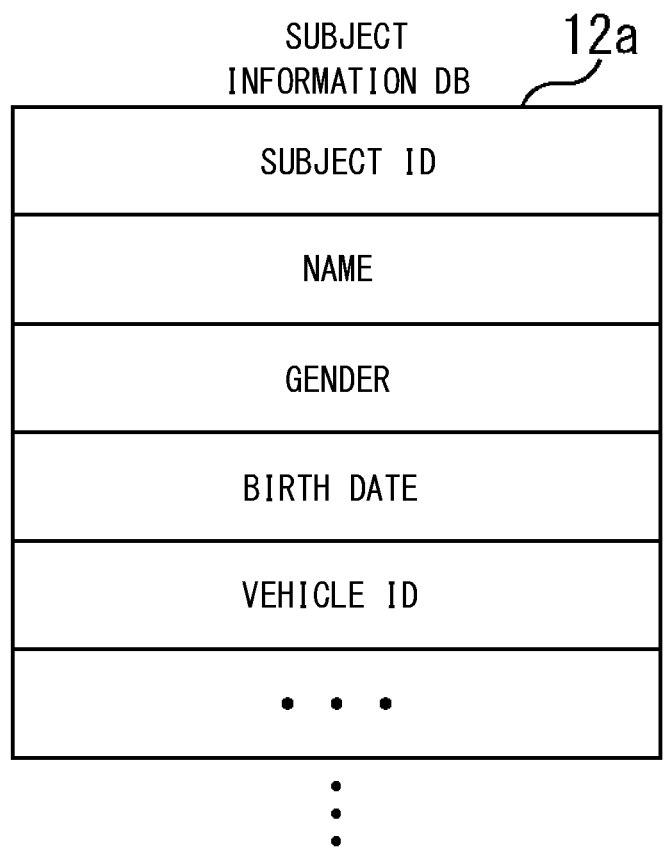
FIG. 3 is a diagram showing an example of data stored in a subject information database in FIG. 2.
Figure 4:
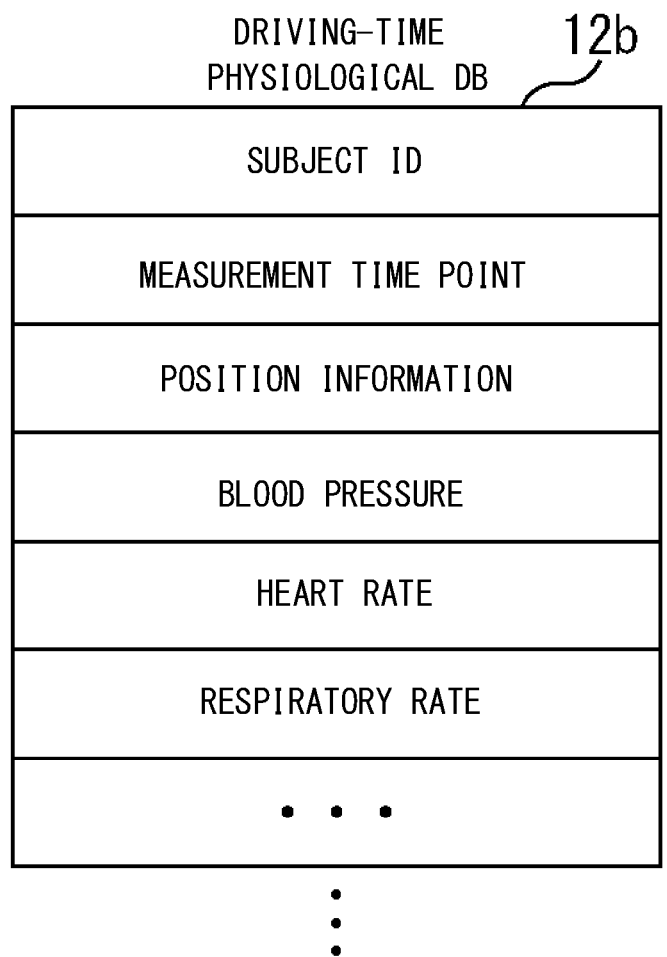
FIG. 4 is a diagram showing an example of data stored in a driving-time physiology database in FIG. 2.
Figure 5:
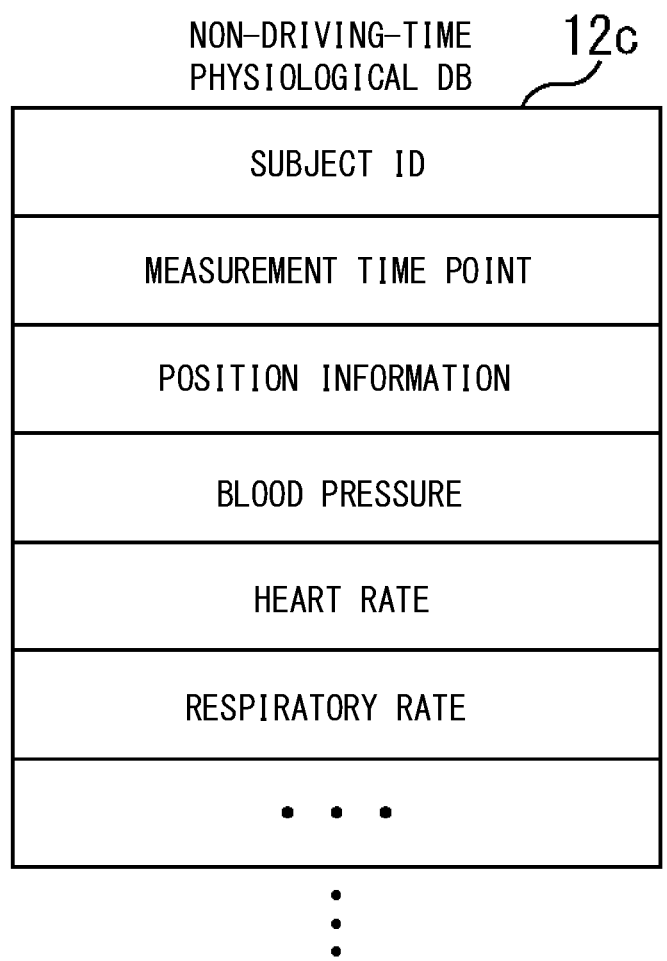
FIG. 5 is a diagram showing an example of data stored in a non-driving-time physiology database in FIG. 2.
Figure 6:
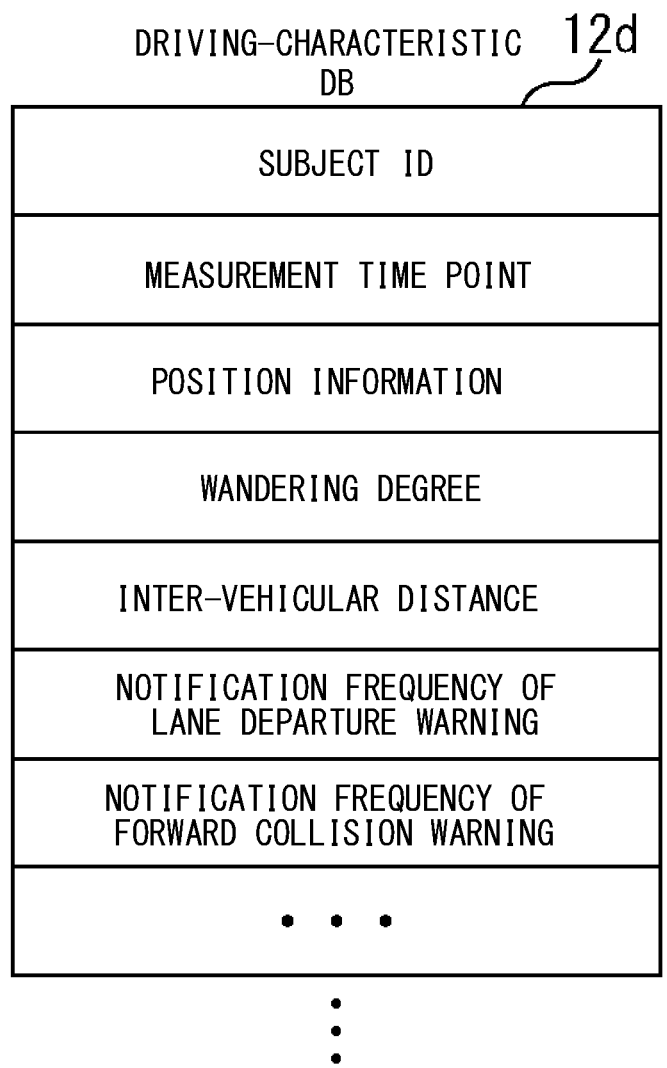
FIG. 6 is a diagram showing an example of data stored in a driving-characteristic database in FIG. 2.
Figure 7:
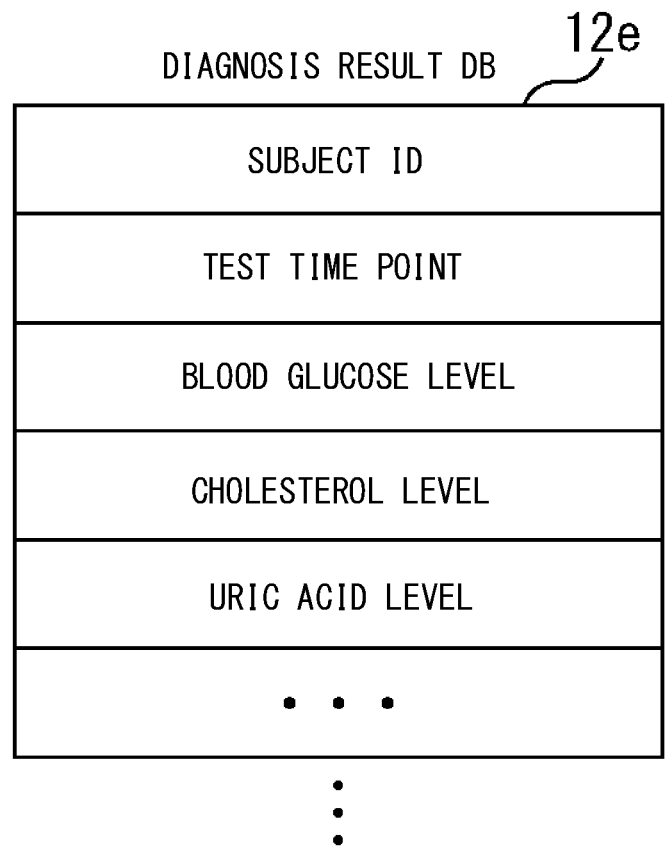
FIG. 7 is a diagram showing an example of data stored in a health diagnosis database in FIG. 2.
Figure 8:
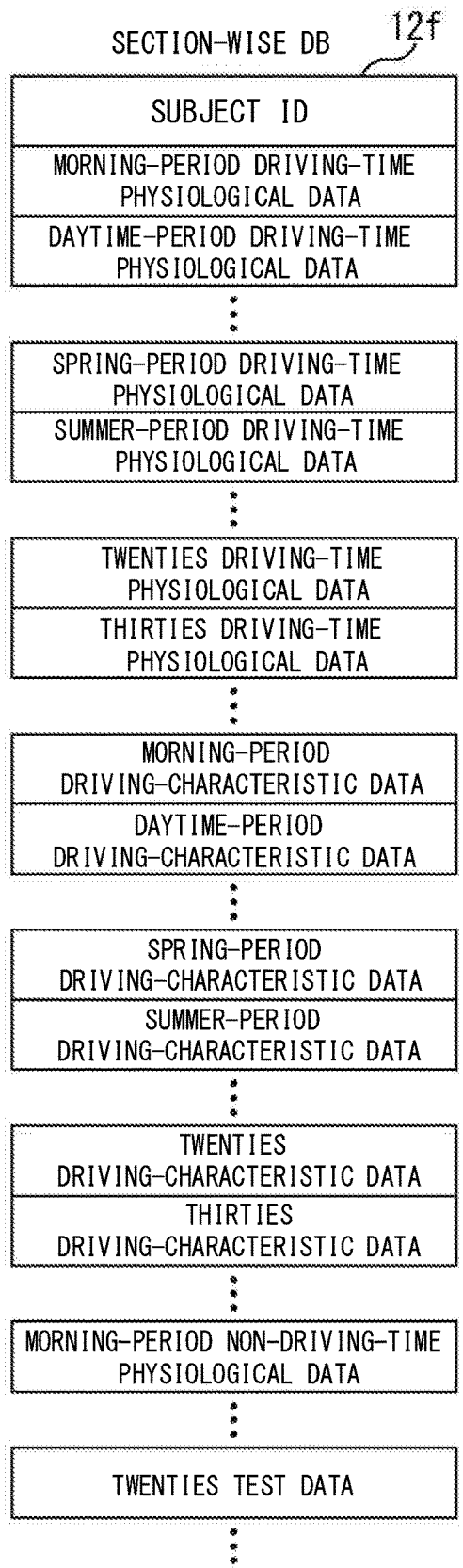
FIG. 8 is a diagram showing an example of data stored in a section-wise database in FIG. 2.
Figure 9:
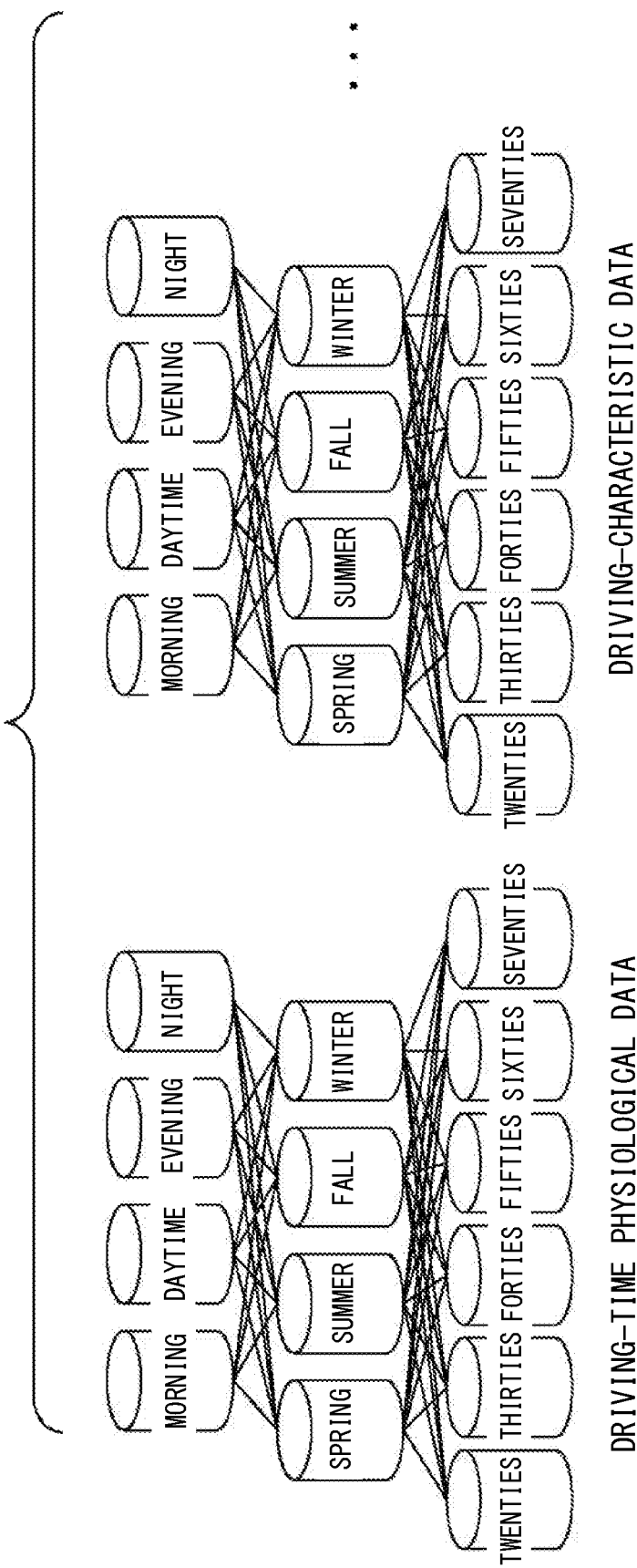
FIG. 9 is a schematic diagram showing an example of the section-wise database in FIG. 8.

FIG. 2 is a block diagram schematically showing an example configuration of an information processing server device 10. FIG. 3 is a diagram showing an example of data stored in a subject information database. FIG. 4 is a diagram showing an example of data stored in a driving-time physiology database. FIG. 5 is a diagram showing an example of data stored in a non-driving-time physiology database. FIG. 6 is a diagram showing an example of data stored in a driving-characteristic database. FIG. 7 is a diagram showing an example of data stored in a health diagnosis database. FIG. 8 is a diagram showing an example of data stored in a section-wise database. FIG. 9 is a schematic diagram showing an example of a section-wise database.

As shown in FIG. 2, the physiological-condition assessing server device 10 includes a communication unit 11, a storage unit 12, an output unit 13, an input unit 14, an input/output interface unit 15, and a control unit 16. The control unit 16 and the input/output interface unit 15 are connected electrically via a system bus 17. In addition, the physiological-condition assessing server device 10 has a clock function.

The communication unit 11 connects to the network N electrically or electromagnetically and controls the state of communications with, for example, the mobile terminal device 20.

The storage unit 12 includes, for example, hard disk drives or solid state drivers. The storage unit 12 stores, for example, physiological data of each subject T. The storage unit 12 stores various programs, such as an operating system and server programs, and various files. Incidentally, the various programs may be available from, for example, another server device over the network N, or may be recorded in a recording medium and read via a drive device.

In the storage unit 12, a subject information database 12a (hereinafter, simply a "subject information DB 12a"), a driving-time physiological database 12b (hereinafter, simply a "driving-time physiological DB 12b"), a non-driving-time physiological database 12c (hereinafter, simply a "non-driving-time physiological DB 12c"), a driving-characteristic database 12d (hereinafter, simply an "driving-characteristic DB 12d"), a diagnosis result database 12e (hereinafter, simply a "diagnosis result information DB 12e"), a section-wise database 12f (hereinafter, simply a "section-wise DB 12f"), and other databases are created. The subject information DB 12a stores, for example, information concerning each of the subjects T. The driving-time physiological DB 12b stores, for example, physiological data of each subject T who is driving the vehicle V. The non-driving-time physiological DB 12c stores, for example, physiological data of each subject T who not is driving the vehicle V. The driving-characteristic DB 12d stores, for example, driving characteristics of each subject T who is driving the vehicle V. The diagnosis result DB 12e stores, for example, diagnosis results of the subject T in the medical institutions. The section-wise DB 12f stores, for example, driving-time physiological data classified by time zone (an example of the first period or the second period) such as morning, daytime and nigh, season (an example of the first period or the second period) such as spring, summer, fall and winter, etc.

Herein, an example of the first period or the second period includes, for example, a morning period (for example, 6:00-10:00), a daytime period (for example, 10:00-15:00), an evening period (for example, 15:00-19:00) and a night period (for example, 19:00-6:00), in which one day is divided into four in time. Examples of the time zone such as morning, daytime, evening and night may include, for example, the morning period (for example, one hour before sunrise-10:00), the daytime period (for example, 10:00-one hour before sunset), evening period (for example, one hour before sunset-one hour after sunset) and night period (for example, one hour after sunset-one hour before sunrise).

In addition, an example of the first period or the second period may include a time zone in which one day is divided into eight in time, for example, a before-dawn period (for example, 0:00-3:00), a dawn period (for example, 3:00-6:00), a morning period (for example, 6:00-9:00), a before-noon period (for example, 9:00-12:00), an after-noon period (for example, 12:00-15:00), an evening period (for example, 15:00-18:00), a beginning-of-night period (for example, 18:00-21:00), or a late-night period (for example, 21:00-0:00).

The first period or the second period may include a time section corresponding to human biorhythm. The section of the first period or the second period may not be equally spaced.

An example of the first period or the second period may include a section in second unit, a section in tens of minutes unit, or a section in tens of hours unit. The first or second period may be changed depending on length of driving time after starting driving (may be after a break) or disease and physical condition to be determined. For example, as the driving time increases, the period of the first period or the second period may be extended, such as from every second unit to every several hours.

An example of the first period or the second period may include a section in week unit, a section in month unit, and a section in year unit.

An example of the first period or the second period may include a section in season. For example, it may be a section according to four seasons such as spring, summer, autumn and winter, a section such as summer-winter, or a section of season such as rainy season and dry season. The section of season may be twenty-four sections of the solar year or seventy-two sections of the solar year. According to the solar calendar or lunar calendar, the season may be classified. Based on summer solstice and winter solstice, the season may be classified. An example of the first period or the second period may include the first week or the second week of a certain month, etc.

As shown in FIG. 3, the subject information DB 12a stores, for example, a name of the subject T, the gender, the birth date, and the vehicle ID used by the subject T, in association with the subject ID for identifying each subject T.

As shown in FIG. 4, the driving-time physiological DB 12b (an example of the first storage means, an example of the fourth storage means) stores, for example, measurement time points when the physiological data was measured while the subject T is driving the vehicle V, position information of the subject T, and the physiological data such as blood pressure value, heart rate and respiratory rate of the subject T etc., in association with each subject ID.

Herein, the physiological data may be biological, chemical and physical data of the subject T measurable by sensors etc. For example, an example of the physiological data includes, for example, body temperature and body temperature distribution of the subject T. An example of the physiological data includes, for example, data that is blood and cardiovascular relationship like blood pressure value, heart rate, pulse wave, pulse wave propagation speed, electrocardiogram, arrhythmia state, blood flow rate, and blood components such as blood glucose level. Examples of the blood components include, for example, red blood cell count, white blood cell count, platelet count, pH value, electrolyte type, electrolyte quantity, hormone type, hormone quantity, and uric acid value, various markers.

In addition, an example of the physiological data includes, for example, amount of perspiration, distribution of perspiration, resistance value of skin, component of body odor, amount of digestive liquid such as saliva amount, components of digestive liquid such as saliva components. An example of the physiological data includes, for example, data on brain such as electroencephalogram, brain blood flow distribution, etc. An example of the physiological data includes, for example, data on respiration such as respiratory rate, respiratory volume, expiratory components, etc.

An example of the physiological data includes, for example, data on eyes such as number of blinks, amount of tears, eye movement (eyeball position, pupil diameter, etc.), etc. An example of the physiological data includes, for example, myoelectric data of each part of the body. An example of the physiological data includes, for example, data of facial color, facial expressions, etc.

An example of the physiological data includes, for example, physiological data on sleeping such as bedtime, wakeup time, sleeping time, sleeping pattern, snoring or not, strength of snoring, number of snoring, time of snoring, state of breathing, number of turns, posture during sleep, sleep quality like sleeping depth, etc. The sleep quality may be determined from, for example, the electroencephalogram, the eye movement, the breath, the posture during sleep, etc.

An example of the physiological data includes, for example, weight and height. In addition, an example of the physiological data may include numerical data of symptoms of pain, numbness, etc.

In addition, an example of the measurement time point includes, for example, a time point when the measurement was started, a time point when the measurement was completed, or an intermediate time point between them. The measurement time point may be a time point corresponding to measurement of a certain value. For example, in the case that heart rate is calculated every minute, it may be any time point in this one minute. In addition, examples of such time point include the peak time point of the R wave, the time point of the Q wave or the S wave, the peak time point of the P wave, etc. in the case of calculating the heart rate from the length of time between the R waves in the electrocardiogram. Instead of time between R waves, it may be time between P waves, Q waves, S waves, or T waves. In addition, not only in the electrocardiogram but also in graph of pulse waves, it may be a time point at which common characteristic points appear or an intermediate value as well. In addition, in case that blood pressure is measured by the Korotkoff sound, the measurement time point may be any time point within the measurement period when calculating the maximal blood pressure and the minimal blood pressure.

As shown in FIG. 5, the non-driving-time physiological DB 12c (an example of the second storage) stores, for example, a measurement time point measuring physiological data when the subject T is not driving the vehicle V, position information of the subject T, and physiological data such as blood pressure value, heart rate, respiration rate, etc. of the subject T, in association with each subject ID. Examples of time when the subject T is not driving the vehicle V include, for example, a case that the subject T is at home H (such as when the subject T is sleeping, relaxing, working, etc.), a case that the subject T is working in the workplace, a case that the subject T is on board in spite of not driving the vehicle V, a case that the subject T is walking outside, and a case that the subject T is on another vehicle.

Incidentally, the physiological data may be stored in the storage unit 12 with driving-time or non-driving-time tags (additional information) without separating into the driving-time physiology DB 12b and the non-driving-time physiological DB 12c.

As shown in FIG. 6, the driving-characteristic DB 12d (an example of the third storage) stores, for example, a measurement time point measuring driving-characteristic data when the subject T is driving the vehicle V, position information of the vehicle V, wandering degree of the steering wheel, inter-vehicular distance, etc., in association with each subject ID.

Herein, An example of the driving-characteristic data includes, for example, wandering degree of turning angle in the steering wheel, value or fluctuation of inter-vehicular distance (or inter-vehicular time), the number of times and frequency (notification frequency of forward collision warning) of approach to vehicles traveling ahead (for example, if the inter-vehicle time is within 3 seconds, within 1 second, etc.), distance from place of momentary stop line when stopping, and the number or frequency of deviations from the road (notification frequency of lane deviation warning). In addition, driving-characteristic data may be fluctuation of the speed of the vehicle V, the number and frequency of sudden braking (the number and frequency of decelerations greater than or equal to the predetermined value), time from when the brake is required to when the brake pedal is stepped, etc. It may be data on which the maneuverability of the subject T can be measured.

As shown in FIG. 7, diagnosis result DB 12e stores, for example, a test time point testing each subject T, and test data such as blood glucose level, cholesterol level, and uric acid level, in association with each subject ID.

These test data such as blood glucose level, cholesterol level, and uric acid level are accurately measured by examination organizations.

Examples of the diagnosis result include various test results to be determined from blood test, images taken by X-rays, images measured by ultrasonic echo, images measured by nuclear magnetic resonance apparatus, and inquiry results of doctors.

As shown in FIG. 8, section-wise DB 12f stores, for example, statistic of the driving-time physiological data, statistic of the driving-characteristic data, statistic of the non-driving-time physiological data, and statistic of the test data, for the section of each time zone, the section of season and the section of age, in association with each subject ID.

For example, in the section-wise DB 12f, a period driving-characteristic data in time zone obtained by statistically processing the driving-time physiological data of the measurement time point belonging to each time zone, a period driving-characteristic data in season obtained by statistically processing the driving-time physiological data of the measurement time point belonging to each season, and an age-period driving-characteristic data obtained by statistically processing the driving-time physiological data of the measurement time point belonging to each age.

Herein, examples of statistic include, for example, representative values in the section such as average (arithmetic mean, geometric mean, harmonic mean, median, mode, maximum value, minimum value, etc.), dispersion, standard deviation, skewness, flatness, etc.

An example of the period-data (the period driving-time physiological data, the period non-driving-time physiological data, or the period driving-characteristic data) includes, for example, separate multiple data such as period physiological data in the first period and period physiological data in the second period, or period physiological data in the first period and the second period. An example of the period physiological data in the first period and the second period includes, for example, period physiological data calculated from data belonging to a certain time zone (for example, morning, night, etc.) and belonging to a certain season (for example, spring, summer, etc.), period physiological data calculated from data belonging to a certain time zone (for example, morning, night, etc.) and belonging to a certain age (for example, 2010, 2015, etc.), and period physiological data calculated from data belonging to a certain season zone (for example, spring, summer, etc.) and belonging to a certain age (for example, 2010, 2015, etc.).

In addition, the first period or the second period may not be exactly the same period for each period data. For example, the first period may be the morning period, the measurement time point of the non-driving-time physiological data may be 6:00 am to 7:30 am, and the measurement time point of the driving-time physiological data may be 7:45 am to 9:00 am. The period non-driving-time physiological data corresponding to at least one of the first period and the second period may be any statistic of non-driving-time physiological data of which measurement time point belongs to at least one of the first period and the second period.

As shown in FIG. 9, section-wise DB 12f includes data structure unit divided for each section of time zone, each section of season, and each section of age, corresponding to the type of data such as a driving-time physiological data, a driving-characteristic data, a non-driving-time physiological data, a test data.

Upon acquiring the data, the statistics of the corresponding data structure unit are recalculated and the statistics are updated, according to the measurement time point and the type of data.

Incidentally, the data structure unit may be constructed for each subject T, and for each data structure unit, the statistics may be stored in association with the subject ID.

The physiological-condition assessing server device 10 may calculate statistics of the physiological data and driving-characteristic data by collecting subjects having common gender, age, constitution, etc. according to the section, and store them in the section-wise DB 12f.

In addition, the section of the section-wise DB 12f may be changed according to the driving time. For example, initially, the physiological-condition assessing server device 10 averages data every second unit, accumulates data in the section-wise DB 12f, and captures time-series changes. Then, as the driving time increases, it may change the length of the averaging period of the section from the average of every second unit to every minute, every several ten minutes, every few hours, etc.

The subject information DB 12a, driving-time physiological DB 12b, non-driving-time physiological DB 12c, driving-characteristic DB 12d, diagnosis result DB 12e and section-wise DB 12f may exist in the physiological-condition assessing server device 10, exist in another server connected to the physiological-condition assessing server device 10 via a network, or be distributed in the network N. These may be separate databases, or be in the same database.

The first storage means, the second storage means, the third storage means and the fourth storage means may be in the same database.

The output units 13 has, for example, liquid crystal display elements or electroluminescence (EL) devices in case of outputting image. The output units 13 has speakers in case of outputting sound.

The input unit 14 has, for example, a keyboard and a mouse.

The input/output interface unit 15 conducts interface processing between the communication unit 11 and the memory unit 12 etc., and the control unit 16.

The control unit 16 has, for example a CPU (Central Processing Unit) 16a, a ROM (Read Only Memory) 16b, and a RAM (Random Access Memory) 16c. When the CPU 16a reads and executes various programs stored in the ROM 16b or the memory unit 12, the control unit 16 assesses physiological condition of each subject T.

The RAM 16c may functions as an example of the first storage means, the second storage means, the third storage means or the fourth storage means. Especially, in the case that the first period or the second period is several seconds unit, several minutes unit or several hours unit, the physiological data and the driving-characteristic data may be stored in the RAM 16c temporarily.

(2.2 Configuration and Functions of Mobile Terminal Device 20)

Figure 10:
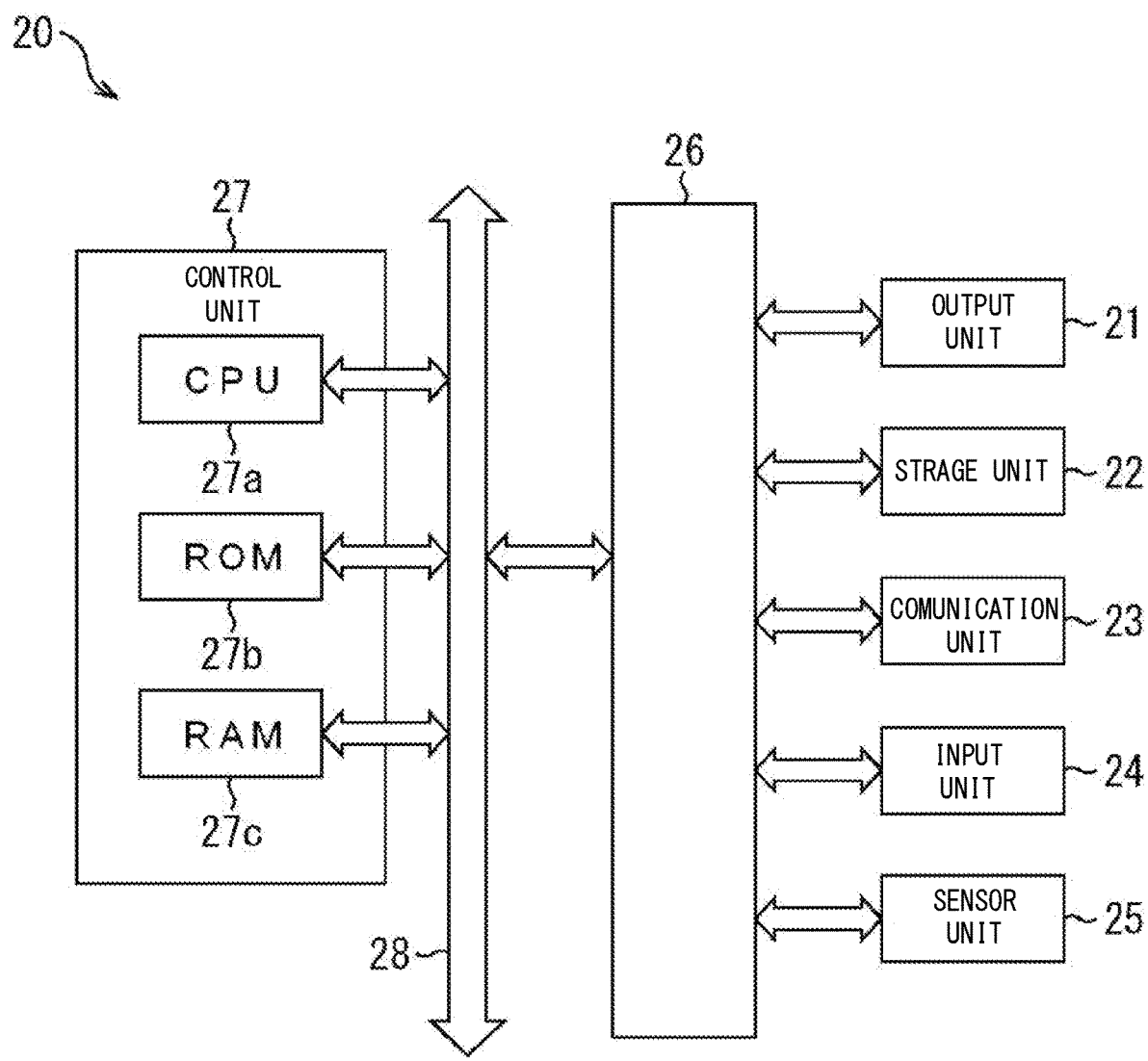
FIG. 10 is a block diagram schematically showing an example configuration of a mobile terminal device in FIG. 1.
Figure 11:
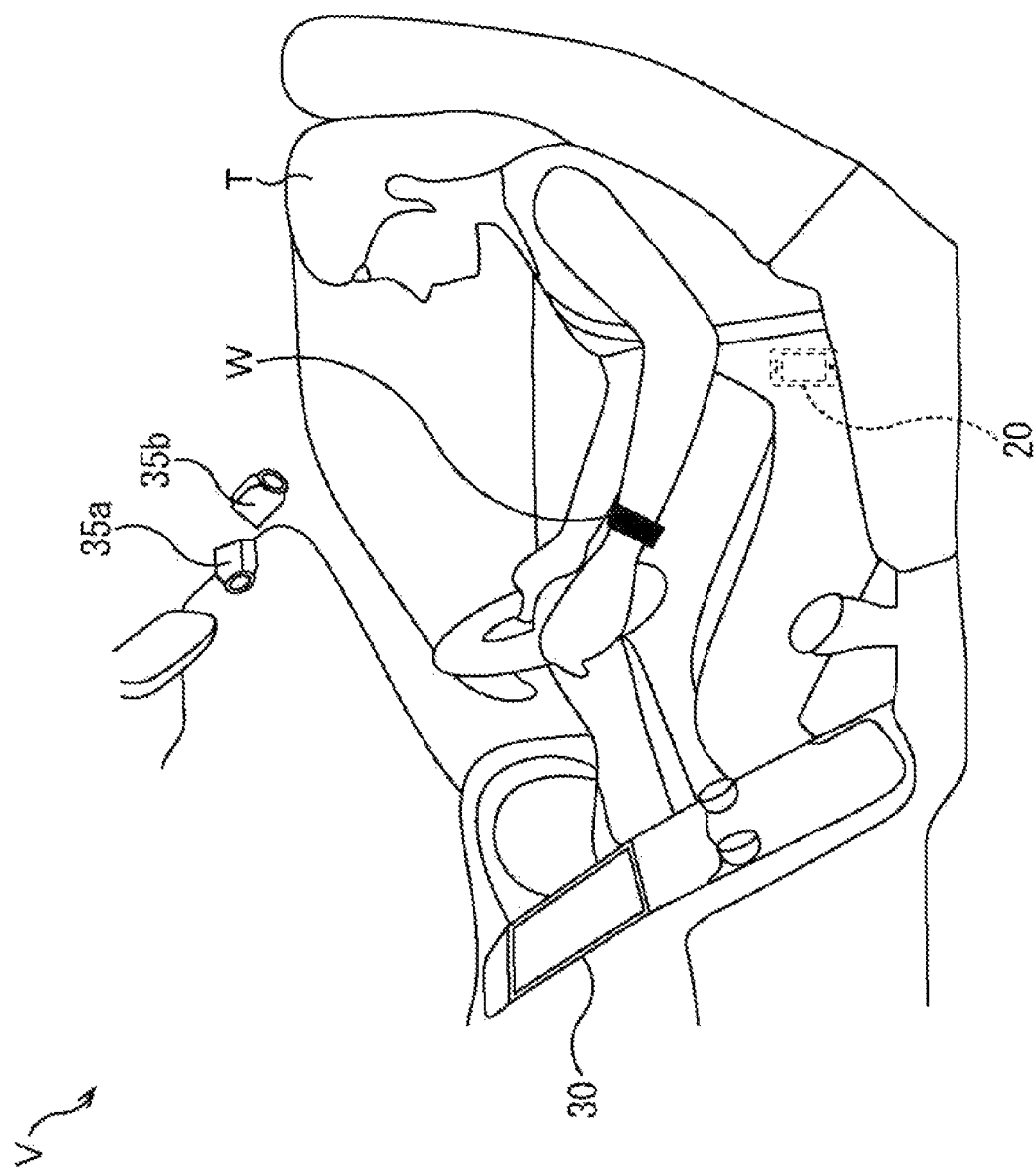
FIG. 11 is a schematic diagram showing an example of appearance of a subject steering a vehicle.

The following describes a configuration and functions of the mobile terminal device 20 using FIG. 10 and FIG. 11.

FIG. 10 is a block diagram schematically showing an example configuration of the mobile terminal device 20. FIG. 11 is a schematic diagram showing an example of appearance of the subject T steering the vehicle V.

As shown in FIG. 10, the mobile terminal device 20 includes an output unit 21, a storage unit 22, a communication unit 23, an input unit 24, a sensor unit 25, an input/output interface unit 27 and a control unit 27. The control unit 27 and the input/output interface unit 26 are connected electrically via a system bus 28. In addition, each mobile terminal device 20 is assigned a mobile terminal ID. The mobile terminal device 20 has a clock function. The mobile terminal device 20 may have a vibration function for vibrating the mobile terminal device 20.

The output unit 21 has, for example, a liquid crystal display element or an EL element as a display function. The output unit 32 has a speaker that outputs sound.

The storage unit 22 includes, for example, hard disk drives or solid state drivers. The storage unit 22 stores various programs such as an operating system and apps for the mobile terminal device 20. Incidentally, the various programs may be available from, for example, another server device over the network N, or may be recorded in a recording medium and read via a drive device.

The communication unit 23 connects to the network N electrically or electromagnetically and controls the state of communications with, for example, the physiological-condition assessing server device 10. In addition, the communication unit 23 connects to the physiological-condition assessing server device 10 electrically or electromagnetically and controls the state of communications with, for example, the physiological-condition assessing server device 10.

The communication unit 23 has a function of wireless communication for conducting communication with a terminal device by radio waves or infrared rays. The mobile terminal device 20 communicates with the in-vehicle terminal device 30 and the home terminal device 40 via the communication unit 23. In addition, as shown in FIG. 11, a wearable terminal device W worn by the subject T and the mobile terminal device 20 carried by the subject T communicate via the communication unit 23. Incidentally, the mobile terminal device 20 may conduct wired communication with the in-vehicle terminal device 30, the home terminal device 40 and the wearable terminal device W.

The communication unit 23 may communicate with IC tags as a leader of the IC tags.

The input unit 24 has, for example, a display panel of a touch switch type such as a touch panel. The input unit 24 acquires position information of the output unit 21 to which the user's finger touched or approached. The input unit 24 has a microphone for inputting sound.

The input unit 24 accepts input of medication information such as the presence or absence of taking medication and the kind of medicine.

The sensor unit 25 has various sensors such as a GPS (Global Positioning System) sensor, a direction sensor acceleration sensor, a gyro sensor, an atmospheric pressure sensor, a temperature sensor and a humidity sensor. The sensor unit 25 has imaging elements such as a CCD (Charge Coupled Device) image sensor and a CMOS (Complementary Metal Oxide Semiconductor) image sensor of a digital camera. The mobile terminal device 20 acquires current position information of the mobile terminal device 20 by the GPS sensor.

The mobile terminal device 20 may read medicine information of medicine packaging or prescription with the camera of the sensor unit 25, or read medication information of the pasted IC tag by the reader of the IC tag.

The input/output interface unit 25 conducts interface processing between the output unit 21 and the memory unit 22 etc., and the control unit 27.

The control unit 27 includes a CPU 27a, a ROM 27b, and a RAM 27c. In the control unit 27, the CPU 27a reads and executes various programs stored in the ROM 27b or the storage unit 22.

Herein, the wearable terminal device W is a wearable computer. The wearable terminal device W has an output unit, a storage unit, a communication unit, an input unit, a sensor unit, an input/output interface unit, a control unit and a timer unit (not shown).

The sensor unit of the wearable terminal device W measures various physiological data of the subject T.

The sensor unit has a temperature sensor, a pressure sensor, an ultrasonic sensor, a light sensor, an electric sensor, a magnetic sensor, an image sensor, etc.

The temperature sensor measures the temperature of contacted parts.

The pressure sensor measures, for example, pulse waves.

The light sensor detects responses of irradiating the skin, etc. with electromagnetic waves, that is, at least one of a reflected wave and a transmitted wave. The light sensor measures the velocity of blood flow, blood components, etc.

The ultrasonic sensor detects responses irradiated with ultrasonic waves, that is, at least one of a reflected wave and a transmitted wave.

The electric sensor measures voltage, current, impedance, etc. The electric sensor measures electric field generated by muscle work, blood flow, nerve excitation, etc. The electric sensor also detects components of sweat, etc. by combining with electrodes, and functions as a chemical sensor, a pH sensor, etc.

The magnetic sensor measures the magnetic field generated by muscle work, blood flow, nerve excitation, etc.

The image sensor detects the color of skin, the surface temperature, the movement of the surface, the flow of blood flow, the appearance of sweat, etc.

In addition, the sensor unit has a GPS sensor, a direction sensor, an acceleration sensor, a gyro sensor, an atmospheric pressure sensor. The wearable terminal device W may measure the posture during sleeping, the number of turns, the number of steps, the moving distance, the exercise amount, etc. by these sensors.

In addition, the microphone of the input unit may capture sleeping breath and respiratory sound of the subject T.

The physiological data measured by the sensor unit of the wearable terminal device W is transmitted to the mobile terminal device 20 via the communication unit. Incidentally, the wearable terminal device W may transmit the measured physiological data to the in-vehicle terminal device 30.

Incidentally, as a type of the wearable terminal device W, it may be a glasses type, a finger ring type, a shoe type, an in-pocket type, a necklace type, a garment type, etc.

(2.3 Configuration and Functions of In-Vehicle Terminal Device 30)

Figure 12:
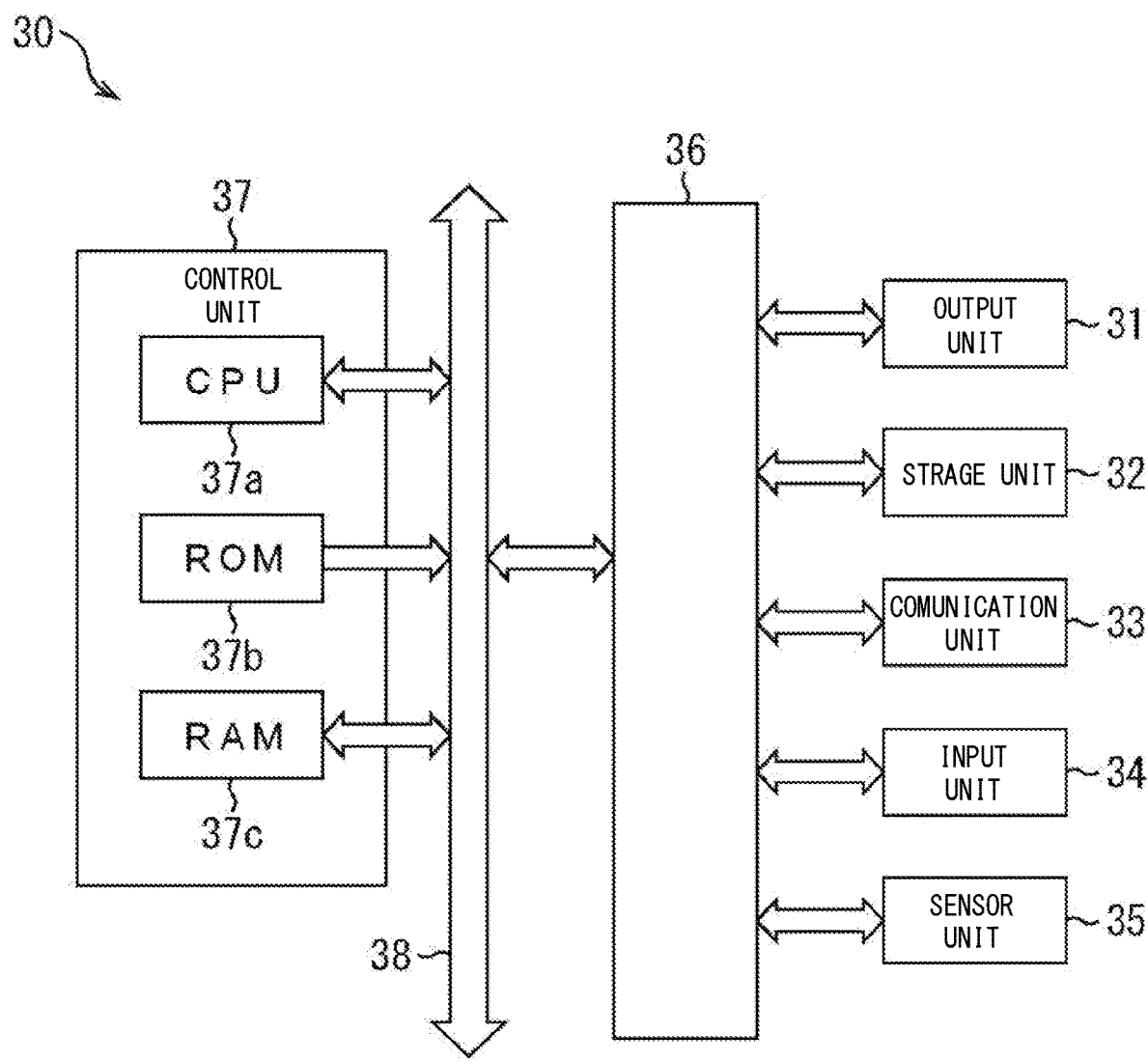
FIG. 12 is a block diagram schematically showing an example configuration of an in-vehicle terminal device in FIG. 1.

The following describes a configuration and functions of the in-vehicle terminal device 30 using FIG. 12.

FIG. 12 is a block diagram schematically showing an example configuration of the in-vehicle terminal device 30.

As shown in FIG. 12, the in-vehicle terminal device 30 includes an output unit 31, a storage unit 32, a communication unit 33, an input unit 34, a sensor unit 35, an input/output interface unit 36, and a control unit 37. The control unit 37 and the input/output interface unit 36 are connected electrically via a system bus 38. In addition, each in-vehicle terminal device 30 is assigned a vehicle ID. The in-vehicle terminal device 30 has a clock function.

As shown in FIG. 11, the in-vehicle terminal device 30 is, for example, a navigation device mounted on the vehicle V.

The output unit 31 has, for example, a liquid crystal display element or an EL element as a display function, and a speaker that outputs sound.

The storage unit 32 includes, for example, hard disk drives or solid state drivers. The storage unit 32 stores various programs such as an operating system and apps for the in-vehicle terminal device 30. Incidentally, the various programs may be available from, for example, another server device over the network N, or may be recorded in a recording medium and read via a drive device.

The storage unit 32 has map information for navigating the vehicle V.

The communication unit 33 connects to the network N electrically or electromagnetically and controls the state of communications with, for example, the physiological-condition assessing server device 10. In addition, the communication unit 33 connects to the physiological-condition assessing server device 10 electrically or electromagnetically and controls the state of communications with, for example, the physiological-condition assessing server device 10. The communication unit 33 controls communication with the mobile terminal device 20 by wireless communication.

The communication unit 33 communicates with the drive mechanism of the vehicle V. For example, a control signal is transmitted to the drive mechanism of the vehicle V via the communication unit 33 of the in-vehicle terminal device 30, and the vehicle V is stopped, stopped at a predetermined place, and navigated to a predetermined place such as a hospital.

The input unit 34 has, for example, a display panel of a touch switch type such as a touch panel. The input unit 34 acquires position information of the output unit 31 to which the user's finger touched or approached. The input unit 34 has a microphone for inputting sound.

The sensor unit 35 has various sensors such as a GPS sensor, a direction sensor acceleration sensor, a gyro sensor, an atmospheric pressure sensor, a temperature sensor and a humidity sensor. The sensor unit 35 has an angle sensor for measuring the operation angle in the steering wheel. The sensor unit 35 has imaging elements such as a CCD image sensor and a CMOS image sensor of a digital camera.

The GPS sensor acquires the current position information of the vehicle V.

As shown in FIG. 11, the sensor unit 35 has a camera 35a and a camera 35b.

The camera 35a photographs external circumstances from the vehicle V. From the image of the camera 35a, the in-vehicle terminal device 30 measures the inter-vehicle distance, measures the stop position, measures lane departure, measures the condition of the road surface (presence or absence of rain, presence or absence of snow, presence or absence of pavement, etc.), and measures the presence or absence of a human.

The camera 35b photographs subject T. From the image of the camera 35b, the in-vehicle terminal device 30 authenticates the subject T with facial recognition, measures the facial color of the subject T, and determines whether the subject T is dozing.

The input/output interface unit 36 conducts interface processing between the output unit 31 and the memory unit 32 etc., and the control unit 37.

The control unit 37 includes a CPU 37a, a ROM 37b and a RAM 37c. In the control unit 37, the CPU 37a reads and executes various programs stored in the ROM 37b or the storage unit 32.

(2.4 Configuration and Functions of Home Terminal Device 40)

Figure 13:
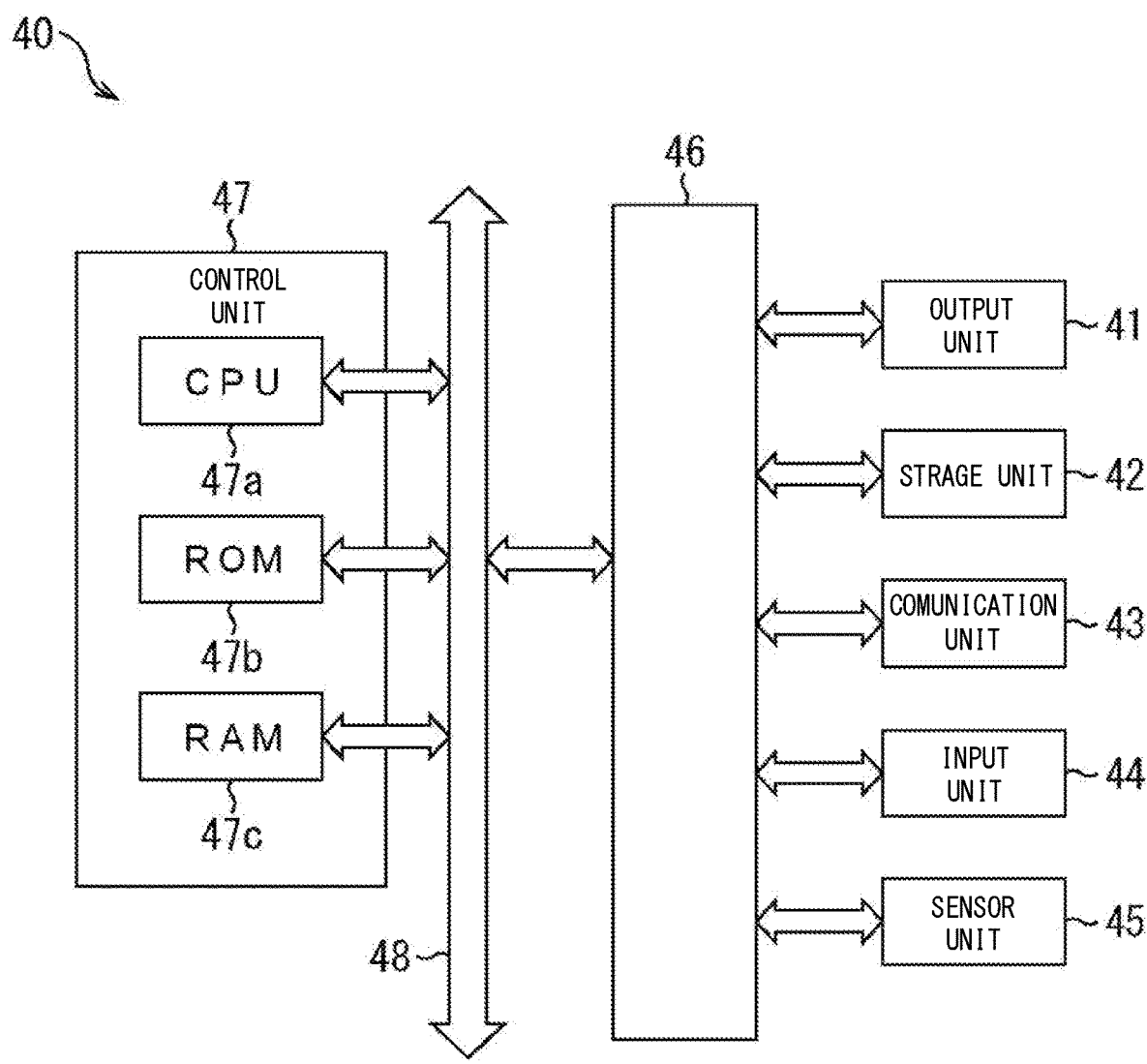
FIG. 13 is a block diagram schematically showing an example configuration of a home terminal device in FIG. 1.

The following describes a configuration and functions of the home terminal device 40 using FIG. 13. In addition, configurations and functions substantially similar to those of the mobile terminal device 20, etc. will be omitted.

As shown in FIG. 13, the home terminal device 40 includes an output unit 41, a storage unit 42, a communication unit 43, an input unit 44, a sensor unit 45, an input/output interface unit 46 and a control unit 47. The control unit 47 and the input/output interface unit 46 are connected electrically via a system bus 48. In addition, each home terminal device 40 is assigned a home terminal ID. The home terminal device 40 has a clock function.

As with the communication unit 23, the communication unit 43 may communicate with the wearable terminal device W to acquire physiological data. The communication unit 43 may communicate with the mobile terminal device 20 to receive or transmit the physiological data.

The sensor unit 45 may be a camera placed in the home H. This camera may photograph the sleeping state of the subject T and behavior in the room (presence or absence of taking medication, etc.) as the physiological data.

The home terminal device 40 transmits the collected physiological data to the physiological-condition assessing server device 10.

(2.5 Configuration and Functions of Medical Institution Server Device 50)

Figure 14:
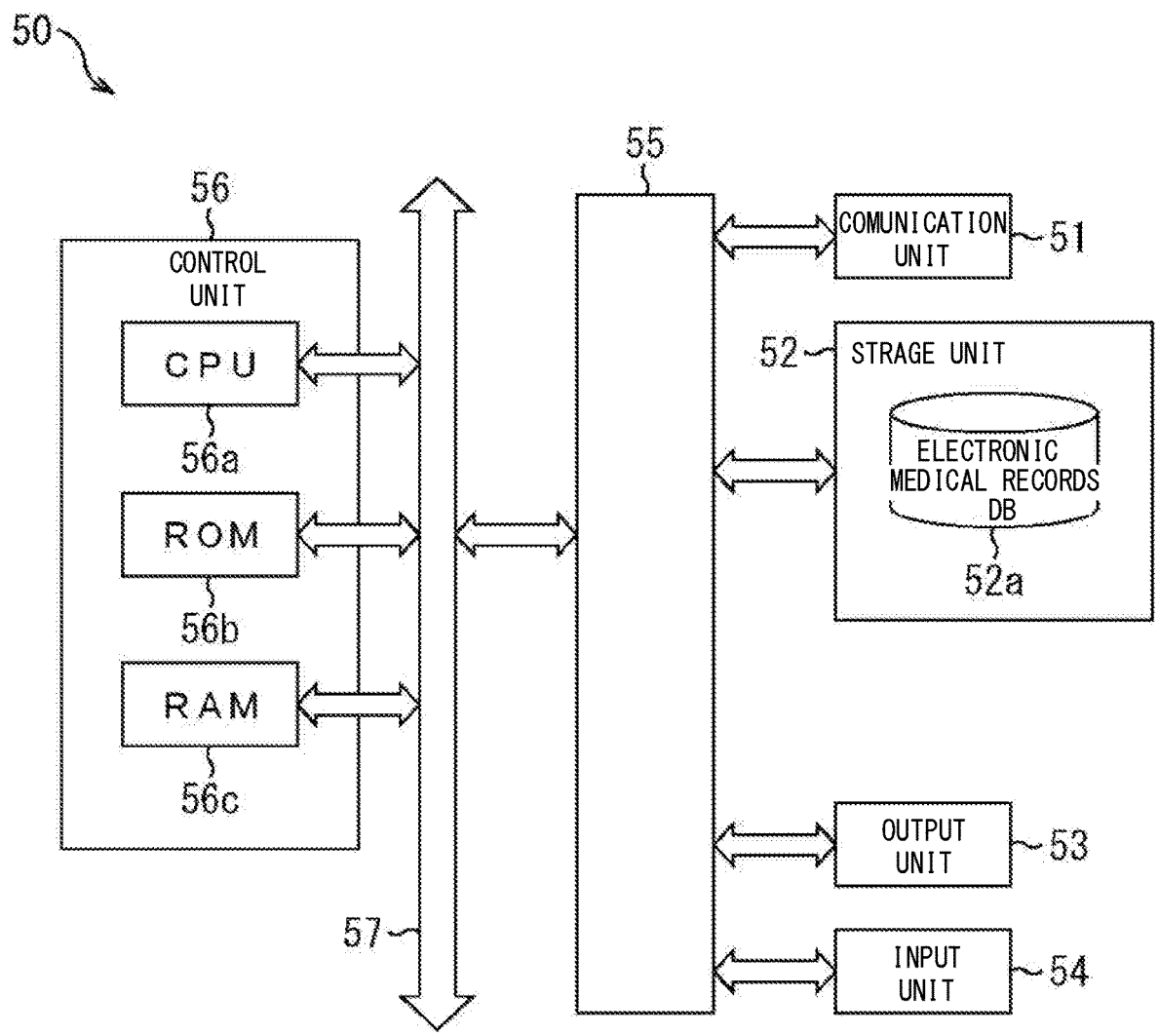
FIG. 14 is a block diagram schematically showing an example configuration of a medical institution server device in FIG. 1.
Figure 15:
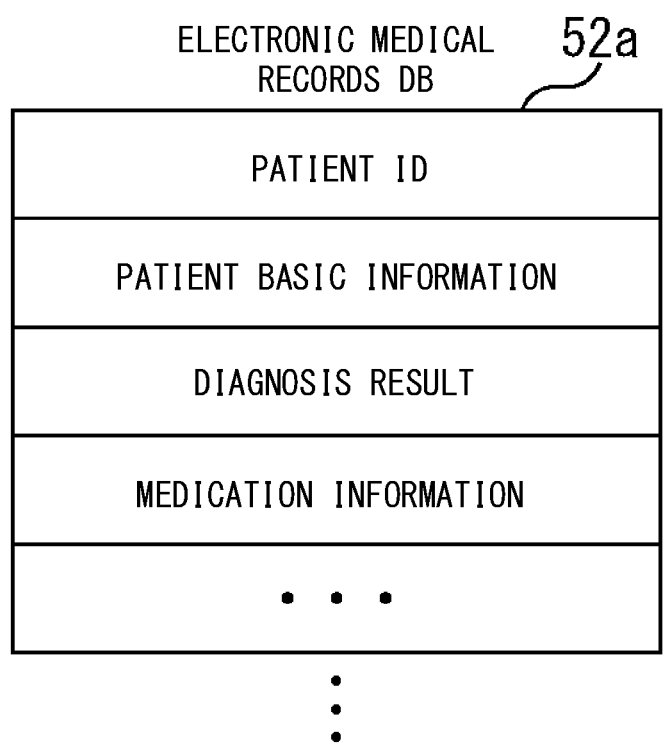
FIG. 15 is a diagram showing an example of data stored in an electronic medical records database in FIG. 14.

The following describes a configuration and functions of the medical institution server device 50 using FIG. 14 and FIG. 15. In addition, since it has almost the same configurations and functions as the physiological-condition assessing server device 10, etc., different configurations and functions will mainly be described.

FIG. 14 is a block diagram schematically showing an example configuration of the medical institution server device 50. FIG. 15 is a diagram showing an example of data stored in the electronic medical records database.

As shown in FIG. 14, the medical institution server device 50 includes a communication unit 51, a storage unit 52, an output unit 53, an input unit 54, an input/output interface unit 55 and a control unit 56. The control unit 56 and the input/output interface unit 55 are connected electrically via a system bus 57. In addition, the medical institution server device 50 has a clock function.

The storage unit 52 has an electronic medical records DB 52a.

As shown in FIG. 15, the electronic medical records DB 52a stores, for example, patient basic information such as name, gender, age, etc., diagnosis result of the subject T like the diagnosis result DB 12e, and medication information such as name do drug to be medicated to the subject T, the dosage, the medication time point and doctor in charge, in association with patient ID for identifying each subject T.

The medical institution server device 50 transmits the diagnosis result, etc. of the subject T to the physiological-condition assessing server device 10 in response to a request from the physiological-condition assessing server device 10.

(2.6 Functional Block of Physiological-Condition Assessing Device 10)

Figure 16:
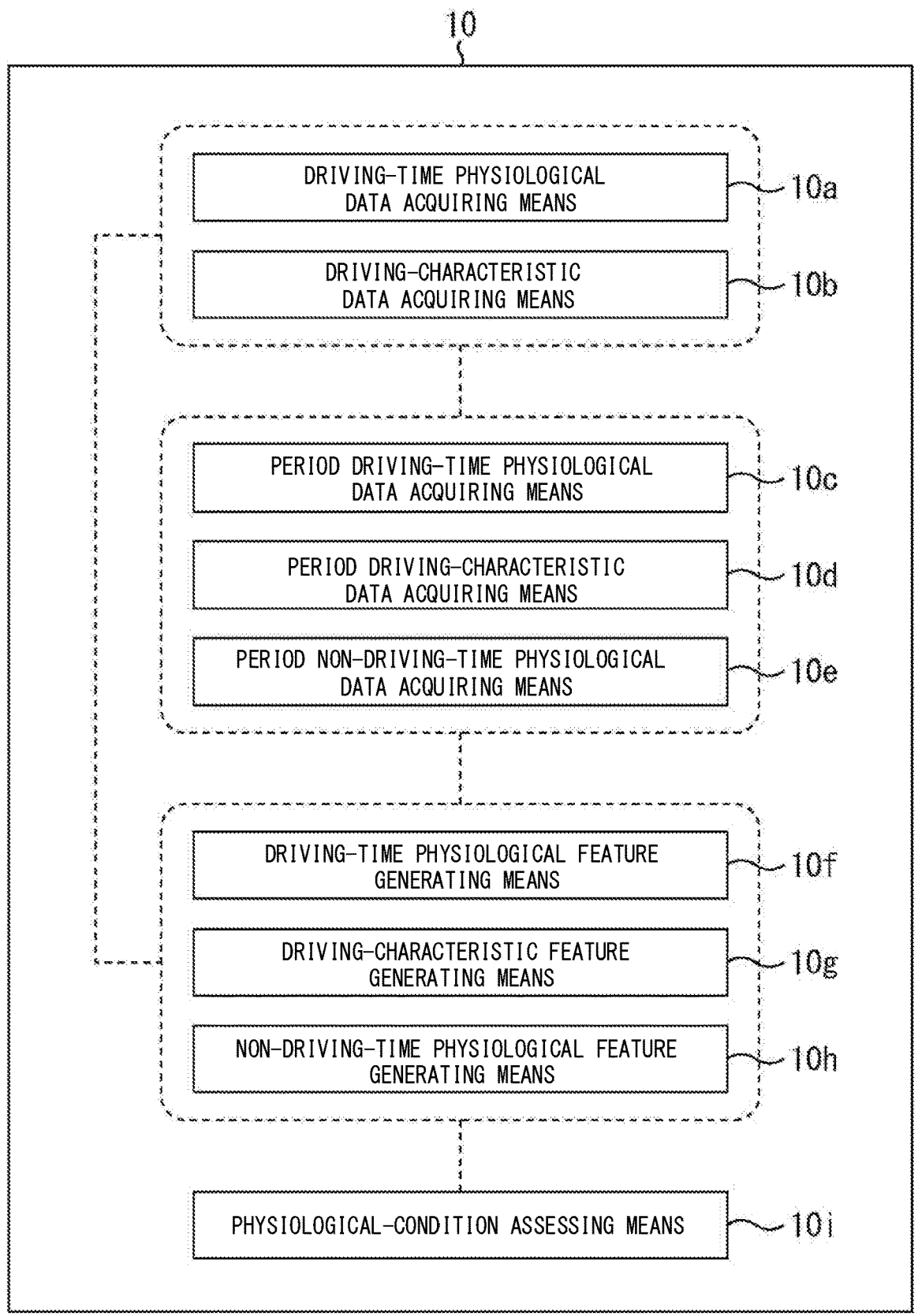
FIG. 16 is a block diagram showing an example of function of the information processing server device.

The following describes a functional block of physiological-condition assessing device 10 using FIG. 16.

FIG. 16 is a block diagram showing an example of function of the information processing server device 10.

As shown in FIG. 16, the physiological-condition assessing server device 10 includes a driving-time physiological data acquiring means 10a, a driving-characteristic data acquiring means 10b, a period driving-time physiological data acquiring means 10c, a period driving-characteristic data acquiring means 10d, a period non-driving-time physiological data acquiring means 10e, a driving-time physiological feature generating means 10f, a driving-characteristic feature generating means 10g, a non-driving-time physiological feature generating means 10h and a physiological-condition assessing means 10i.

The driving-time physiological data acquiring means 10a acquires a driving-time physiological data of a subject measured when the subject is driving a vehicle, and a measurement time point of the driving-time physiological data.

Herein, examples of the vehicle V include, for example, an automobile such as passenger car, taxis, hire, truck, trailer (including tractor alone) and bus, a motorcycle (side motorized motorcycle, trike, reverse trike), bicycle, electric cart, train like a train car.

Examples of subject T include, for example, a person driving the vehicle.

The driving-characteristic data acquiring means 10b acquires a driving-characteristic data indicating a driving characteristic in which the subject drives the vehicle, and a measurement time point of the driving-characteristic data.

The period driving-time physiological data acquiring means 10c acquires a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means (for example, the driving-time physiological DB 12b or the section-wise DB 12f) for storing the driving-time physiological data measured in the past. The period driving-time physiological data may be acquired by calculation from the driving-time physiological data from the driving-time physiological DB 12b, or may be acquired from the section-wise DB 12f.

The period driving-characteristic data acquiring means 10d acquires a period driving-characteristic data corresponding to the first period and the second period, with reference to a second storage means (for example, the driving-characteristic DB 12d or the section-wise DB 12f) for storing the driving-characteristic data measured in the past. The period driving-characteristic data may be acquired by calculation from the driving-time physiological data from the driving-characteristic DB 12d, or may be acquired from the section-wise DB 12f.

The period non-driving-time physiological data acquiring means 10e acquires a period non-driving-time physiological data corresponding to at least one of the first period and the second period, with reference to a third storage means (for example, the non-driving-time physiological DB 12c or the non-driving-time physiological DB 12c) for storing a non-driving-time physiological data measured in the past that is the physiological data of the subject when the subject is not driving the vehicle. The period non-driving-time physiological data may be acquired by calculation from the driving-time physiological data from the non-driving-time physiological DB 12c, or may be acquired from the section-wise DB 12f.

The driving-time physiological feature generating means 10f generates a driving-time physiological feature indicating feature of the physiological data of the subject while driving, from the driving-time physiological data and the period driving-time physiological data.

An example of the driving-time physiological feature includes the difference (subtraction, ratio, degree of difference, etc.) between each received driving-time physiological data (present value) and each period driving-time physiological data (the subject T's blood pressure, heart rate, respiratory rate, etc. on driving day, blood pressure, heart rate, respiratory rate, etc. in recent days, and the subject T's blood pressure, heart rate, respiratory rate, etc., in the period such as morning, spring, etc.) in the first period or the second period, in case that the first period or the second period is a driving day (for example, a period such as second unit, several minutes unit, or several hours unit), a relatively short period (from a few days to several weeks longer than the driving day), a period such as morning, daytime, evening and night, and a seasonal period.

Herein, the current value, which is the value of the measurement time point of the data such as the driving-time physiological data and the driving-characteristic data, may be the value of the received data itself, the value averaged over several seconds unit, or the value averaged over several minutes unit.

In addition, the driving day which is an example of the first period or the second period is the day to which the measurement time point belongs. In addition, in case that the measurement time point is the time when the date changes like the near midnight, the driving day does not have to be the same day, it may belong to any day.

The value on the driving day (an example of the period driving-time physiological data, an example of the period driving-characteristic data or the period non-driving-time physiological data) may be a statistic including the current value (the current value of the period driving-time physiological data, the current value of the period driving-characteristic data, or the current value of the period non-driving-time physiological data) or a statistic not including the current value. In the case of the statistic that does not include the current value in the value of the driving day, it will be easy to capture the change, and in the case of the statistic that includes the current value in the value of the driving day, it is difficult to be influenced by abnormal values.

An example of the value of the driving day may be a trend on the driving day. For example, the trend on the driving day is calculated from moving average in several seconds to hours unit, or exponential smoothing corresponding to several seconds to several hours unit.

In addition, for the period in the driving day, the length of time averaged may be changed according to the length of driving time and the disease or physical condition to be assessed. For example, as the driving time gets longer, the average time length may be longer, such as every minute, every tens of minutes, every few hours, from the average per second unit.

For the trend on the driving day, each time a certain time elapses such as every minute, every five minutes, every ten minutes, . . . from the start of driving, a time series trend may be output by conducting processing such as moving average in coarser time unit.

As the driving time becomes longer, stable trend data with small fluctuation range can be obtained by increasing the moving average window width, so that risk assessing accuracy when comparing with current value is improved.

Each period driving-time physiological data in the first period or the second period may be a value obtained by moving average or exponential smoothing.

Considering the time lag of moving average or exponential smoothing, it may be a difference from each received driving-time physiological data.

The value in a relatively short period (an example of the period driving-time physiological data, an example of the period driving-characteristic data or the period non-driving-time physiological data) may be a statistic including the current value or a statistic not including the current value.

As an example of the value in a relatively short period may be a trend in a relatively short period. For example, the trend in a relatively short period is calculated from moving average or exponential smoothing corresponding to the relatively short period.

In addition, an example of the driving-time physiological feature includes the slope of change over time (an example of the amount of change over time) of each period driving-time physiological data in a relatively long time, or the degree of difference (an example of the amount of change over time) between each received driving-time physiological data (present value) and the baseline of change over time of each period driving-time physiological data in a relatively long period (for example, a curve approximated by spline interpolation, least squares method, etc., or output by moving average or exponential smoothing), in case that the first period or the second period is a relatively long period (for example, one year, two years, three years, five years, ten years, thirty years, etc.).

Regarding the degree of difference between the baseline and the current value, in addition to simple differences, standard deviation and standard error of data used for the baseline may be compared (multiples etc.). For example, the degree of difference is calculated based on 3σ.

The value in a relatively long period which is an example of the amount of change over time (an example of the period driving-time physiological data, an example of the period driving-characteristic data or the period non-driving-time physiological data) may be a statistic including the current value or a statistic not including the current value.

The driving-characteristic feature generating means 10g generates a driving-characteristic feature indicating feature of the driving characteristic of the subject T while driving, from the driving-characteristic data and the period driving-characteristic data.

An example of the driving-time physiological feature includes the difference (subtraction, ratio, etc.) between each received driving-characteristic data (present value) and each period driving-characteristic data in the first period or the second period (wandering degree, inter-vehicular distance, notification frequency of lane deviation warning, notification frequency of forward collision warning, etc. in the period such as morning, etc., or spring, etc. of the subject T), in case that the first period or the second period is a driving day (for example, a period such as second unit, several minutes unit, or several hours unit), a relatively short period (from a few days to several weeks longer than the driving day), a period such as morning, daytime, evening and night, and a seasonal period.

In addition, an example of the driving-characteristic data includes the slope of change over time of each driving-characteristic data in a relatively long time, or the degree of difference between each received driving-characteristic data (present value) and the baseline of change over time of each period driving-characteristic data in a relatively long period (a curve approximated by spline interpolation, least squares method, etc.), in case that the first period or the second period is a relatively long period (for example, one year, two years, three years, five years, ten years, thirty years, etc.).

The non-driving-time physiological feature generating means 10h generates a non-driving-time physiological feature indicating feature of the physiological data of the subject while not driving, from the period non-driving-time physiological data.

An example of the non-driving-time physiological feature includes the difference (subtraction, ratio, etc.) between each period non-driving-time physiological data in one day a day (statistic such as average value, intermediate value, etc.) and each period non-driving-time physiological data (the subject T's blood pressure, heart rate, respiratory rate, etc.) in the first period or the second period, in case that the first period or the second period is a driving day (for example, a period such as second unit, several minutes unit, or several hours unit), a relatively short period (from a few days to several weeks longer than the driving day), a period such as morning, daytime, evening and night, and a seasonal period.

In addition, an example of the non-driving-time physiological feature includes the slope of change over time of each period non-driving-time physiological data in a relatively long time, or the degree of difference between each period non-driving-time physiological data in one day a day (for example, in the same day as the driving day or in the day close to the driving day such as the previous day) and the baseline of change over time of each period non-driving-time physiological data in a relatively long period (a curve approximated by spline interpolation, least squares method), in case that the first period or the second period is a relatively long period (for example, one year, two years, three years, five years, ten years, thirty years, etc.).

As described above, the features may be amount that indicates the characteristics of physiological data or driving-characteristic data such as the value of the difference from the reference, and the slope of the change over time in each physiological data and each driving-characteristic data.

The physiological-condition assessing means 10*i* assesses a physiological condition of the subject, from the non-driving-time physiological feature and at least one of the driving-time physiological feature and the driving-characteristic feature.

(3.1 Operation Example of Physiological-Condition Assessing System S)

Figure 17:
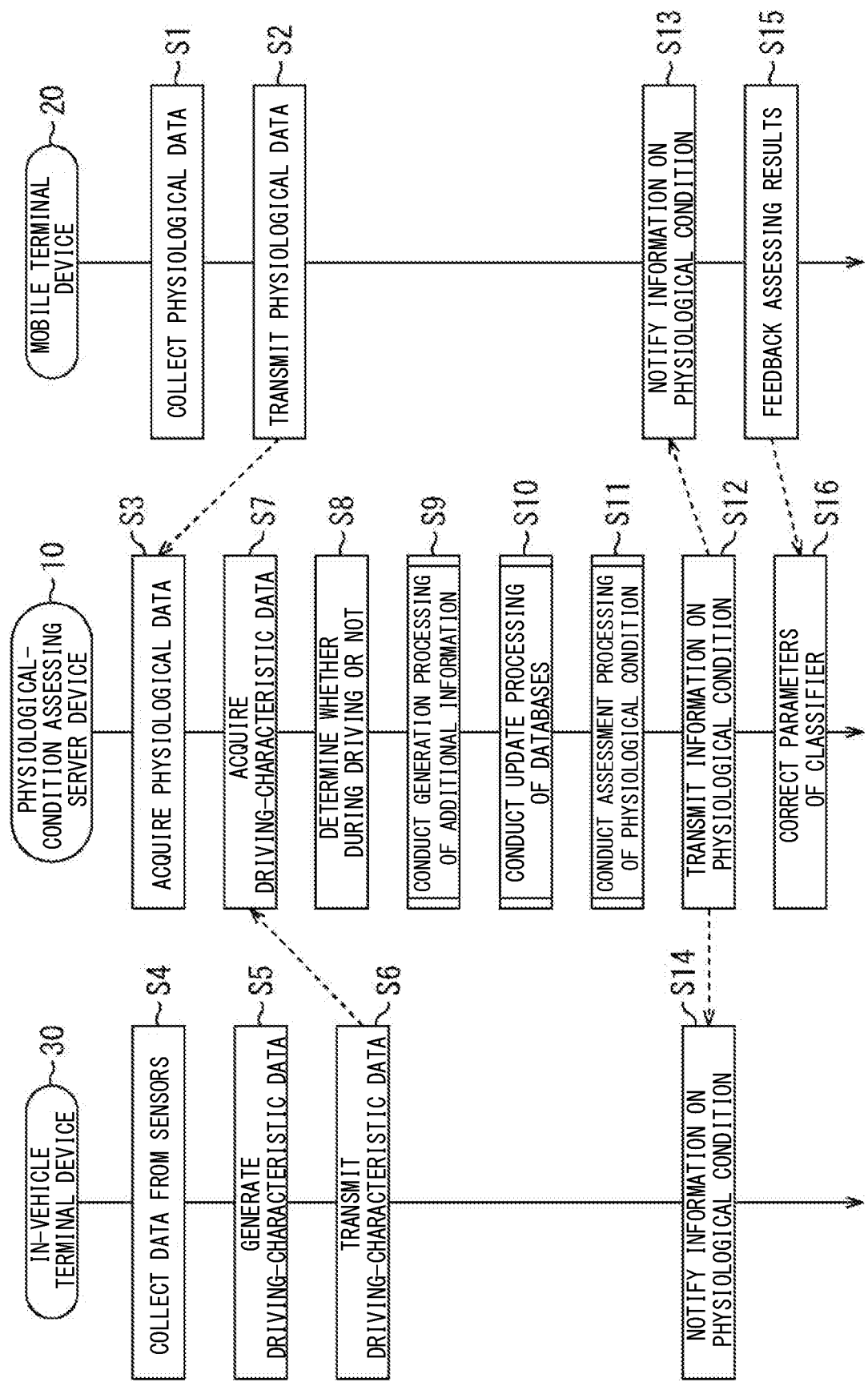
FIG. 17 is a sequence diagram showing an example of operation example of the physiological-condition assessing system according to an embodiment.

The following describes an operation example of physiological-condition assessing system S using FIG. 17.

FIG. 17 is a sequence diagram showing an example of operation example of the physiological-condition assessing system S according to an embodiment.

(3.1.1 Acquisition of Physiological Data)

An acquisition of physiological data of the subject T will be described as the operation example of physiological-condition assessing system S.

The subject T wears the wearable terminal device W on an arm etc. The wearable terminal device W measures the physiological data of the subject T in various living environments, for example, when the subject T is sleeping, eating, walking, working, relaxing, driving the vehicle V, etc. It is assumed that the subject T carries or possesses the mobile terminal device 20 within the distance that it can communicate with the wearable terminal device W. For example, when the mobile terminal device 20 is in the bag while moving, or in the home H or the office, the mobile terminal device 20 may be placed in a predetermined place.

As shown in FIG. 17, the physiological-condition assessing server system S collects, for example, physiological data of the subjects T (Step S1). Specifically, a control unit 27 of a mobile terminal device 20 of a certain subject T acquires physiological data measured by each sensor of a sensor unit 35 of a wearable terminal device W from the wearable terminal device W.

Incidentally, the measurement time point measured by each sensor of the wearable terminal device W may be measured by the clock function of the mobile terminal device 20 or may be measured by the clock function of the wearable terminal device W. When communication between the wearable terminal device W and the mobile terminal device 20 is interrupted, the wearable terminal device W may collectively transmits the physiological data and the measurement time point to the mobile terminal device 20 when communication becomes possible.

In addition, as the environmental information of the subject T, the control unit 27 acquires, in the sensor unit 25, the outside air temperature from the temperature sensor, atmospheric pressure from the atmospheric pressure sensor, humidity from the humidity sensor, current position information from the GPS sensor, etc.

Next, the physiological-condition assessing server system S transmits, for example, the physiological data (Step S2). Specifically, the control unit 27 of a mobile terminal device 20 transmits the various physiological data of the subject T, the measurement time point of the physiological data, the environmental information of the subject T, and the subject ID to the physiological condition assessing server device 10. The control unit 27 may transmit the mobile terminal ID of the mobile terminal device 20 instead of the subject ID.

Incidentally, as the physiological data to be transmitted, the mobile terminal device 20 may transmit the statistic of the physiological data such as an average value obtained by averaging the collected physiological data in a certain time, a value averaged over a predetermined number of times. In the case of sleeping time, the mobile terminal device 20 may transmit at a predetermined time point of the day. Each time physiological data is measured, the mobile terminal device 20 may transmit each physiological data. The mobile terminal device 20 may transmit each physiological data at a predetermined time (for example, every hour, every three hours, or morning, daytime, evening, night etc.). The mobile terminal device 20 may transmit each physiological data separately.

Incidentally, the mobile terminal device 20 may conduct a near field communication with the in-vehicle terminal device 30 and acquire information indicating that the subject T is driving the vehicle V. In this case, the mobile terminal device 20 may transmit the additional information that the physiological data is the driving-time physiological data, to physiological-condition assessing server device 10 together with the measured physiological data.

Next, the physiological-condition assessing server system S acquires, for example, the physiological data (Step S3). Specifically, the control unit 16 of the physiological-condition assessing server device 10 receives the physiological data of the subject T, the measurement time point of the physiological data, and the subject ID, from the mobile terminal device 20 of each subject T.

The control unit 16 may store the received physiological data in the storage unit 12 together with the measurement time point, the position information, etc., in association with subject ID.

In this manner, the physiological-condition assessing server device 10 functions as an example of the driving-time physiological data acquiring means for acquiring a driving-time physiological data of a subject measured when the subject is driving a vehicle, and a measurement time point of the driving-time physiological data.

(3.1.2 Acquisition of Driving-Characteristic Data)

The following describes an acquisition of driving-characteristic data of the subject T in the in-vehicle terminal device 30.

As shown in FIG. 11, the subject T gets on the vehicle V, and the power supply of the in-vehicle terminal device 30 is turned on. The in-vehicle terminal device 30 identifies the driver of the vehicle V. For example, the camera 35*b* of the in-vehicle terminal device 30 may photograph the subject T and conduct face recognition. The in-vehicle terminal device 30 may communicate with the mobile terminal device 20 or the wearable terminal device W of the subject T to identify the driver. The in-vehicle terminal device 30 may identify the driver with the fingerprint recognition sensor on the steering wheel of the in-vehicle terminal device 30. The in-vehicle terminal device 30 may identify the driver by combining these driver identification methods.

When the subject T drives the vehicle V, the in-vehicle terminal device 30 starts measuring the driving-characteristic data.

As shown in FIG. 17, the physiological-condition assessing server system S collects data from sensors (Step S4). Specifically, the control unit 37 of the in-vehicle terminal device 30 acquires the data measured by each sensor of the sensor unit 35 together with the measurement time point of the clock function, from each sensor. For example, the control unit 37 acquires the current position information of the vehicle V, the traveling direction of the vehicle V, the speed, the acceleration, the inter-vehicle distance, the operation angle of the steering wheel, etc., from the sensor of the sensor unit 35. In addition, the control unit 37 acquires the image outside the vehicle V by the camera 35*a*, and acquires the image of the subject T by the camera 35*b*. Incidentally, the measurement time point measured by each sensor of the sensor unit 35 may be measured by the clock function of the in-vehicle terminal device 30.

Next, the physiological-condition assessing server system S generates driving-characteristic data (Step S5). Specifically, the control unit 37 generates driving-characteristic data such as the wandering degree of turning angle in the steering wheel, value or fluctuation of inter-vehicular distance (or inter-vehicular time), based on the data of the sensor unit 35.

The control unit 37 may generate the physiological data of the subject T from the sensor data of the camera 35b, etc.

For example, the control unit 37 generates the physiological data such as the surface temperature of the face and movement of eyes in the subject T.

The control unit 37 may generate driving environment information such as traffic jam situation, state of the road surface, and weather, from the image of the camera 35a.

Next, the physiological-condition assessing server system S transmits, for example, the driving-characteristic data (Step S6). Specifically, the control unit 37 transmits various driving-characteristic data of the subject T, the measurement time point of the driving-characteristic data, and the vehicle ID to the physiological-condition assessing server device 10. The control unit 37 may transmit the subject ID instead of the vehicle ID. The in-vehicle terminal device 30 may transmit ON/OFF of the power supply of the in-vehicle terminal device 30, whether or not the vehicle V is activated, a driving start time point (or driving start signal) that is determined based on the presence or absence of boarding of the subject T, or the driving end time point (or the driving end signal) to the physiological-condition assessing server device 10.

The control unit 37 may transmit the measured physiological data and the generated driving environment information to the physiological-condition assessing server device 10.

Incidentally, as the driving characteristic to be transmitted, the in-vehicle terminal device 30 may transmit the statistic of the driving-characteristic data such as an average value obtained by averaging generated driving-characteristic data in a certain time, and a value averaged over a predetermined number of times. In addition, the in-vehicle terminal device 30 may transmit the driving-characteristic data collectively at a predetermined time (for example, every hour, every three hours), when temporarily stopped, or after the driving ends.

The in-vehicle terminal device 30 may directly transmit the data measured by the sensor to the physiological-condition assessing server device 10. In this case, the physiological-condition assessing server device 10 generates driving-characteristic data from the data of the sensor of the in-vehicle terminal device 30.

Next, the physiological-condition assessing server system S acquires the driving-characteristic data (Step S7). Specifically, the control unit 16 of the physiological-condition assessing server device 10 receives the driving-characteristic data of the subject T, the measurement time point of the driving-characteristic data, and the vehicle ID, from the in-vehicle terminal device 30 of the vehicle V that each subject T is driving.

The control unit 16 stores the received driving-characteristic data, together with the measurement time point, the position information, etc., in the driving-characteristic DB 12d in association with the subject ID.

In this manner, the physiological-condition assessing server device 10 functions as an example of the driving-characteristic data acquiring means for acquiring a driving-characteristic data indicating a driving characteristic in which the subject drives the vehicle, and a measurement time point of the driving-characteristic data.

(3.1.3 Update of Database)

The following describes an update of the databases.

As shown in FIG. 17, the physiological-condition assessing server system S determines whether during driving or not (Step S8). Specifically, the control unit 16 determines whether the physiological data transmitted from the mobile terminal device 20 is physiological data while driving or physiological data while not driving, based on the information from the in-vehicle terminal device 30. More specifically, the control unit 16 determines that the received physiological data is the driving-time physiological data in case that the measurement time point of the physiological data is after the driving start time until the driving end signal (or the driving end time point) is received.

Incidentally, the control unit 16 may determine the received physiological data as the driving-time physiological data in case that the position information where the physiological data was measured and the measurement time point of the physiological data, and the position of the in-vehicle terminal device 30 and the measurement time point of the position are within a predetermined range.

The control unit 16 stores the received physiological data together with the measurement time point, the position information, etc. in the driving-time physiological DB 12b in association with subject ID, in case of being determined to be while driving. The control unit 16 stores the received physiological data together with the measurement time point, the position information, etc. in the non-driving-time physiological DB 12c in association with subject ID, in case of being determined to be while not driving.

Incidentally, the control unit 16 may add additional information on whether it is driving-time or non-driving-time to the physiological data.

The control unit 16 may previously add additional information that the measured physiological data is physiological data while driving in case that the mobile terminal device 20 receives a signal indicating that the mobile terminal device 20 and the in-vehicle terminal device 30 are capable of near field communication and that the subject T is driving in the inside of the vehicle V.

Next, the physiological-condition assessing server system S conducts a generation processing of additional information (Step S9). Specifically, the physiological-condition assessing server device 10 calculates the age to be added to the physiological data, etc. from the birth date of the subject and the measurement time point of the physiological data, etc. The physiological-condition assessing server device 10 generates driving environment information to be added to the physiological data, etc. from the driving environment data based on the measurement time point and the position information. Incidentally, details will be described in a subroutine of the generation processing of additional information.

Next, the physiological-condition assessing server system S conducts an update processing of databases (Step S10). Specifically, the physiological-condition assessing server device 10 selects the sections in the first period and the second period based on the measurement time point.

The physiological-condition assessing server device 10 updates the period driving-time physiological data, the period driving-characteristic data, and the period non-driving-time physiological data in the selected section and age of each period in the section-wise DB 12*f*. Incidentally, details will be described in a subroutine of the update processing.

(3.1.4 Assessing of Physiological Condition)

The following describes an assessing of physiological condition.

As shown in FIG. 17, the physiological-condition assessing server system S conducts an assessment processing of physiological condition (Step S11). Specifically, the physiological-condition assessing server device 10 acquires the driving-time physiological data, the driving-characteristic data, the period driving-time physiological data, the period driving-characteristic data, and the period non-driving-time physiological data corresponding to each period with reference to the section-wise DB 12*f*.

The physiological-condition assessing server device 10 generates the driving-time physiological feature, the driving-characteristic feature, the period driving-characteristic feature, and the non-driving-time physiological feature corresponding to each period The physiological-condition assessing server device 10 selects features according to the physiological condition to be determined. The physiological-condition assessing server device 10 assesses the physiological condition from the selected features by the classifier (for example, a linear classifier or a nonlinear classifier) in the feature space of the features selected according to the physiological condition (for example, each disease) to be assessed. Incidentally, details will be described in a subroutine of the assessment of the physiological condition.

Next, the physiological-condition assessing server system S transmits information on physiological condition (Step S12). Specifically, the control unit 16 transmits the information on physiological condition to the mobile terminal device 20 and the in-vehicle terminal device 30 in case that the control unit 16 assesses the physiological state and needs to notify the subject T. An example of information on physiological condition includes, for example, the level of condition of health, the level of condition of each viscera or organ, the level of condition of each biological function (for example, digestive function, cardiovascular function, function of the nervous system, metabolic function and cognitive function, etc.), a statement that probability of occurrence of predetermined illness has reached a predetermined value or more, the value of the probability of occurrence of predetermined illness, and a statement of the condition of losing health but not a specific disease. In addition, examples of information on physiological condition may include warning information (warning to stop driving, warning to urge medical treatment, etc.) in the case of the health condition level unsuitable for driving the vehicle V. In this case, it may be control information to the in-vehicle terminal device 30 from the control unit 16, such as stopping the vehicle V or reducing the speed.

Next, the physiological-condition assessing server system S notifies the information on physiological condition from the mobile terminal device 20 (Step S13). Specifically, the control unit 27 notifies the subject T of the information on physiological condition by display, voice, etc. from the output unit 21.

Next, the physiological-condition assessing server system S notifies the information on physiological condition to the in-vehicle terminal device 30 (Step S14). Specifically, the control unit 37 notifies the subject T of the information on physiological condition by display, voice, etc. from the output unit 31.

Next, the physiological-condition assessing server system S feedbacks assessing results (Step S15). For example, based on the assessing of the physiological condition, the subject T enters the diagnosis results at the medical examination institution into the mobile terminal device 20. The mobile terminal device 20 transmits the input diagnostic result to the physiological-condition assessing server device 10.

Incidentally, the physiological-condition assessing server device 10 may transmit the results of assessing physiological condition to the medical institution server device 50. After comparing the medical treatment result of the subject T and the assessing result of the physiological-condition assessing server device 10 at the medical institution, the medical institution server device 50 may feedback the comparison result to physiological-condition assessing server device 10.

The feedback of the assessing results may be conducted according to the measured data, the subject T person, an expert such as a doctor in a medical institution, or a combination thereof, depending on the target (type of disease, etc.) to risk assessing. For example, for short-time sleep occurring in sleep apnea syndrome, the feedback of the assessing result may be conducted based on data according to face image, etc. in addition to the judgment of the subject T person. In addition, in case that the risk of occurrence of dangerous arrhythmia is notified, the measurement by the pulse wave or electrocardiogram, etc. may be precisely conducted and the judgment of the doctor, etc. may be fed back based on the measurement result.

Next, the physiological-condition assessing server system S corrects parameters of a classifier (Step S16). Specifically, the control unit 16 corrects the parameters of the discrimination function in the linear classifier or the nonlinear classifier based on the feedback of the assessing result. For example, as a result of the determination based on a certain linear discrimination function, if it is determined that data which should be determined as having risk originally is no risk, the parameters of the linear discrimination function are adjusted so that the data belongs to an discrimination region corresponding to risk in the feature space. When parameters are adjusted so that they can be correctly classified, for example, optimization by the gradient method is conducted.

(3.2 Subroutine of Generation Processing of Additional Information)

Figure 18:
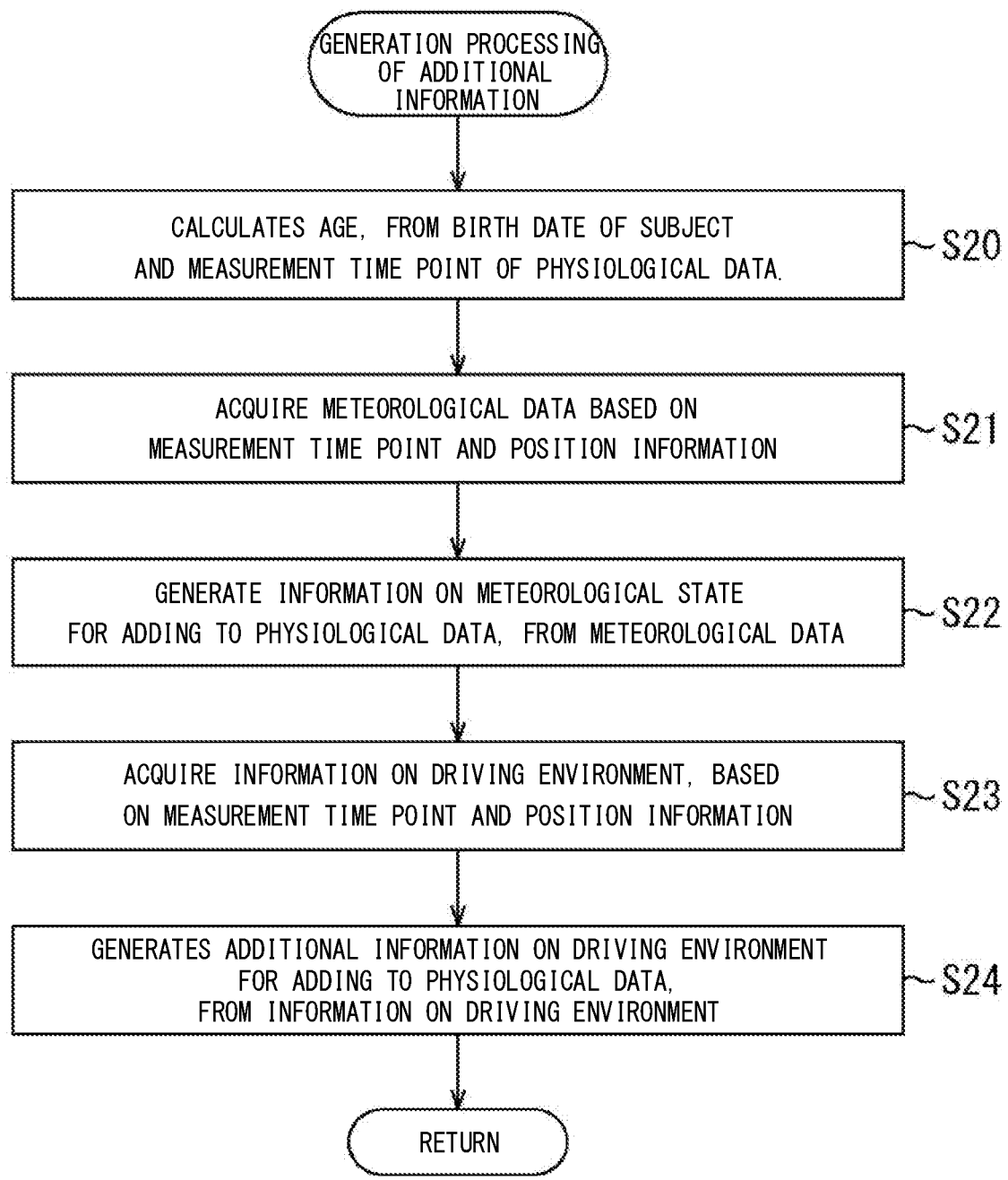
FIG. 18 is a flowchart showing an exemplary subroutine of generation processing of additional information in FIG. 17.

The following describes a subroutine of the generation processing of additional information using FIG. 18.

FIG. 18 is a flowchart showing an exemplary subroutine of generation processing of additional information.

As shown in FIG. 18, the physiological-condition assessing server system S calculates the age, from birth date of the subject T and measurement time point of physiological data, etc. (Step S20). Specifically, the control unit 16 of the physiological-condition assessing server device 10 reads the birth date (an example of birth time) based on the subject ID of the subject T with reference to the subject information DB 12*a* and calculates the age of the subject T at the measurement time from the measurement time point. Incidentally, an example of birth time may include birth year.

Next, the physiological-condition assessing server system S acquires meteorological data based on the measurement time point and the position information (Step S21). Specifically, the control unit 16 transmits the measurement time point of the physiological data and the position information of the measurement location to a meteorological server device, and acquires meteorological data when the physiological data is measured from the meteorological server device. The control unit 16 transmits the measurement time point of the driving-characteristic data and the position information of the measurement location to the meteorological server device and acquires the meteorological data when the driving-characteristic data is measured from the meteorological server device. The meteorological data may be meteorological data measured by the in-vehicle terminal device 30.

Next, the physiological-condition assessing server system S generates information on meteorological state for adding to the physiological data etc., from the meteorological data (Step S22). Specifically, the control unit 16 calculates meteorological state in the first period and the second period. More specifically, the control unit calculates the lowest temperature, the highest air temperature, the lowest air pressure, the average air temperature, the highest air pressure, the average air pressure, the lowest humidity, the highest humidity, the average humidity, etc. in the first period and the second period.

The meteorological state in the first period and the second period may be air temperature, atmospheric pressure, humidity, etc. at a certain time point in the first period and the second period. The meteorological state in the first period and the second period may be weather with long time and weather with many times in the first period and the second period.

The meteorological state in the first period and the second period may be sunshine hours, precipitation amount, wind force, wind direction.

For example, it includes temperature and humidity in a period such as morning on a certain day, and a weather (clear, sunny, slightly cloudy, cloudy, rain, snow, thunder, sandstorm, snowstorm, and fog) determined in a period such as the morning of a certain day. It includes the most frequent weather among weathers of each day in a period such as spring, etc. in a certain year.

Next, the physiological-condition assessing server system S acquires information on driving environment, based on the measurement time point and the position information (Step S23). Specifically, the control unit 16 transmits the measurement time point of the physiological data and the position information of the measurement location to the driving environment provision server device, and acquires the driving environment information when the physiological data is measured from the driving environment provision server device. The control unit 16 transmits the measurement time point of the driving-characteristic data and the position information of the measurement location to the driving environment provision server device, and acquires the driving environment information when the driving-characteristic data is measured from the driving environment provision server device.

Next, the physiological-condition assessing server system S generates additional information on driving environment for adding to the physiological data, etc., from the information on driving environment (Step S24). Specifically, the control unit 16 calculates the driving environment in the first period and the second period. More specifically, the control unit 16 calculates traffic jam situation, state of the road surface, and the number of the approaching people, etc. on the road traveling in the first period and the second period as the driving environments in the first period and the second period. Incidentally, the traffic jam situation may be traffic congestion if the vehicle speed is less than or equal to the predetermined value. The state of the road surface may be calculated from the amplitude and frequency of the vertical vibration of the vehicle V. For example, in case that the amplitude is greater than or equal to the predetermined value, the state of the road surface may be bad.

(3.3 Subroutine of Update Processing of Database)

Figure 19:
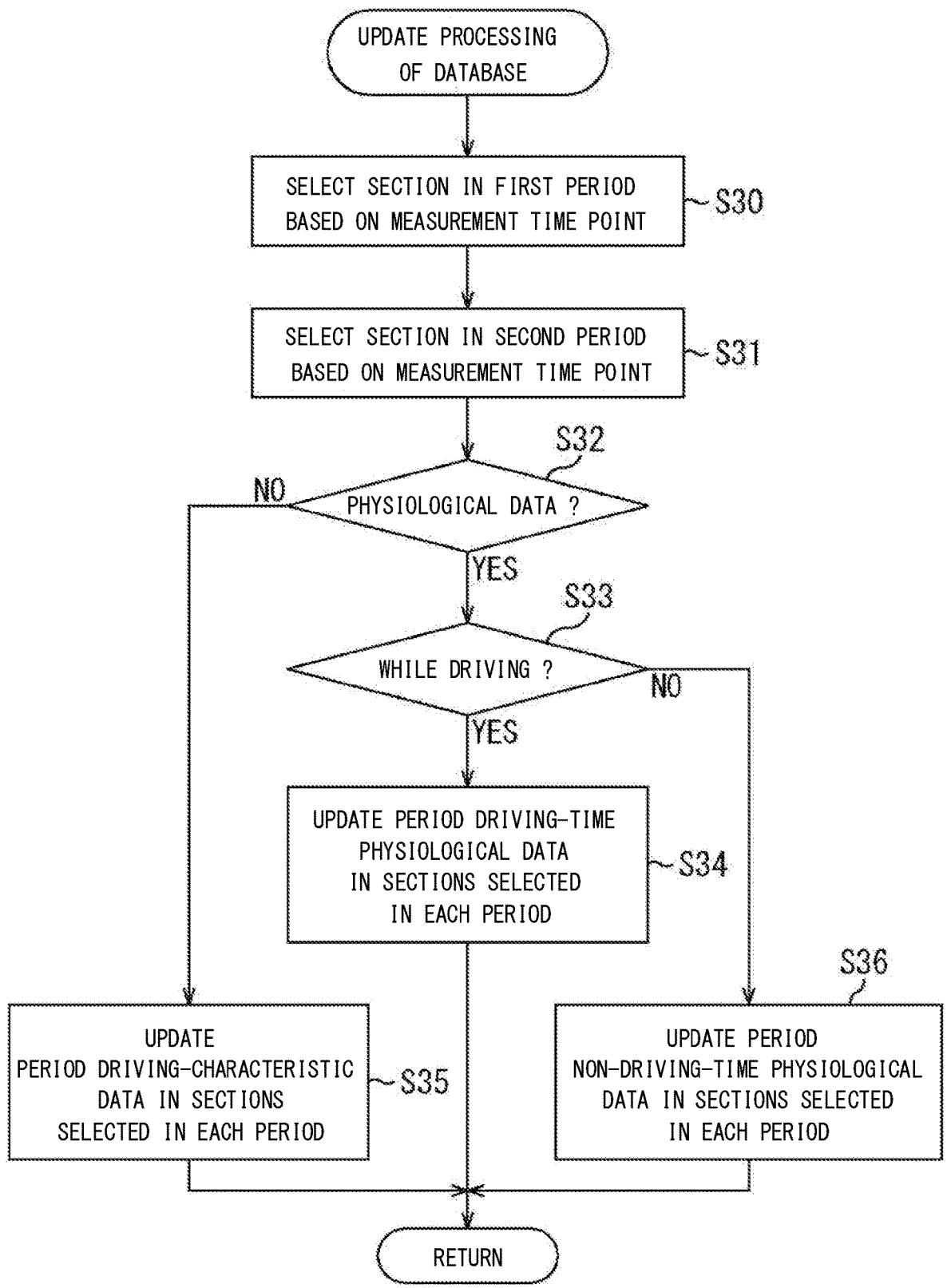
FIG. 19 is a flowchart showing an exemplary subroutine of update processing of database in FIG. 17.

The following describes a subroutine of the update processing of databases using FIG. 19.

FIG. 19 is a flowchart showing an exemplary subroutine of update processing of database.

As shown in FIG. 19, the physiological-condition assessing server system S selects a section in the first period, based on the measurement time point of the data of processing target (Step S30). For example, in case of dividing into four periods of morning, evening, evening and night, the control unit 16 of the physiological-condition assessing server device 10 selects the period to which the measurement time point belongs, that is, the morning-period, the daytime-period, the evening-period or the night-period based on the measurement time point. This first period may be the driving day or a relatively short period.

Next, the physiological-condition assessing server system S selects a section in the second period, based on the measurement time point of the data of processing target (Step S31). For example, in case of dividing into four seasonal periods longer than each period of the four periods of morning, evening, evening, night, the control unit 16 selects the season to which the measurement time point (date of the measurement time point) belongs, that is, the spring-period, the summer-period, the fall-period or the winter-period based on the measurement time point. This second period may be relatively short period for the driving day or relatively long period for a relatively short period.

Next, the physiological-condition assessing server system S determines whether or not it is the physiological data (Step S32). Specifically, the control unit 16 determines whether the data of processing target is physiological data or driving-characteristic data. More specifically, it is determined whether it is physiological data or driving-characteristic data based on information indicating the contents of data such as blood pressure, heart rate, etc. in case of physiological data, or information indicating the contents of data such as wandering, inter-vehicle distance, etc. in case of driving-characteristic data. The control unit 16 may determine the type of data indicating whether it is physiological data or driving-characteristic data by means of a tag attached to the received data.

If it is the physiological data (Step S32; YES), the physiological-condition assessing server system S determines whether or not it is the physiological data while driving (Step S33). Specifically, the control unit 16 determines whether or not it is the physiological data while driving based on the additional information whether it is during driving or not based on additional information while driving or not driving attached to the physiological data. In addition, the control unit 16 may determine from which of the driving-time physiology DB 12b and the non-driving-time physiology DB 12c the data is read, and determine whether or not it is the physiological data while driving.

In the case while driving (Step S33; YES), the physiological-condition assessing server system S updates period driving-time physiological data in the sections selected in each period (Step S34). Specifically, the control unit 16 reads the period driving-time physiological data in the selected first period with reference to the section-wise DB 12f, adds the driving-time physiological data of processing target, recalculates the period driving-time physiological data as a statistic, and stores it in the section-wise DB 12f. The control unit 16 reads the period driving-time physiological data in the selected second period with reference to the section-wise DB 12f, adds the driving-time physiological data of processing target, recalculates the period driving-time physiological data as a statistic, and stores it in the section-wise DB 12f.

Incidentally, the control unit 16 may add the driving-time physiological data of processing target for the period driving-time physiological data matching with additional information such as meteorological conditions, driving environment information, age, etc. attached to the driving-time physiological data of processing target, and may recalculate the period driving-time physiological data as a statistic. Based on the selected first period (or second period), the control unit 16 may store each exercise-time physiological data together with the additional information generated in step S 9 in the section-wise DB 12f.

Based on the first period and the second period (for example, the morning/spring section), the control unit 16 may store each exercise-time physiological data together with the additional information generated in step S 9 in the section-wise DB 12f.

If it is not the physiological data (Step S32; NO), the physiological-condition assessing server system S updates period driving-characteristic data in the sections selected in each period (Step S35). As in step S34, the control unit 16 updates the period driving-characteristic data in the selected section of each period for the driving-characteristic data and the period driving-characteristic data of processing target.

In the case while not driving (Step S33; YES), the physiological-condition assessing server system S updates period non-driving-time physiological data in the sections selected in each period (Step S36). As in step S 34, the control unit 16 updates the period non-driving period physiological data in the selected section of each period for the non-driving-time physiological data and the period non-driving-time physiological data of processing target.

Incidentally, the control unit 16 may update the period driving-time physiological data, the period non-driving-time physiological data, and the period driving-characteristic data corresponding to the age to which the measurement time point of the data of processing target belongs in the section-wise DB 12f.

(3.4 Subroutine of Assessment Processing of Physiological Condition)

Figure 20:
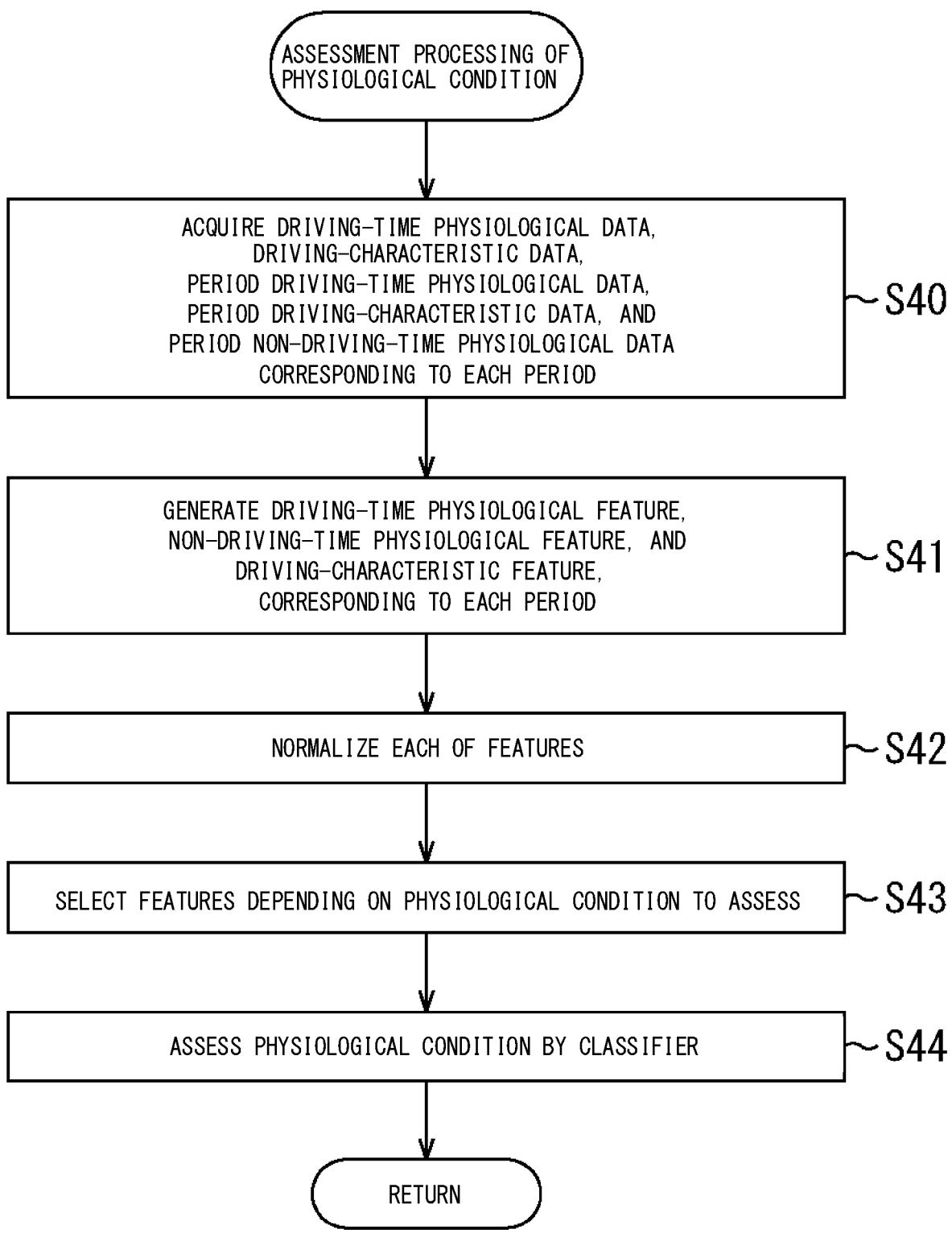
FIG. 20 is a flowchart showing an exemplary subroutine of assessment processing of physiological condition in FIG. 17.

The following describes a subroutine of the assessment processing of physiological condition using FIG. 20.

FIG. 20 is a flowchart showing an exemplary subroutine of assessment processing of physiological condition.

As shown in FIG. 20, the physiological-condition assessing server system S acquires the driving-time physiological data, the driving-characteristic data, the period driving-time physiological, the period driving-characteristic data, and the period non-driving-time physiological data corresponding to each period (Step S40). Specifically, the control unit 16 of the physiological-condition assessing server device 10 acquires the driving-time physiological data, driving-characteristic data, the period driving-time physiological data, period driving-characteristic data, the period non-driving-time physiological data corresponding to the first period or the second period, based on the subject ID of the subject T and the measurement time point of the data with reference to the section-wise DB 12f.

Incidentally, the control unit 16 may calculate the period driving-time physiological data, the period driving-characteristic data, and the period non-driving-time physiological data corresponding to each period, based on the subject ID of the subject T and the measurement time point of the data with reference to the driving-time physiological DB 12b, the non-driving-time physiological DB 12c and the driving-characteristic DB 12d.

In this manner, the physiological-condition assessing server device 10 functions as an example of the period driving-time physiological data acquiring means for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage means for storing the driving-time physiological data measured in the past.

The physiological-condition assessing server device 10 functions as an example of the period driving-characteristic data acquiring means for acquiring a period driving-characteristic data corresponding to the first period and the second period, with reference to a second storage means for storing the driving-characteristic data measured in the past.

The physiological-condition assessing server device 10 functions as an example of the period non-driving-time physiological data acquiring means for acquiring a period non-driving-time physiological data corresponding to at least one of the first period and the second period, with reference to a third storage means for storing a non-driving-time physiological data measured in the past that is the physiological data of the subject when the subject is not driving the vehicle.

Next, the physiological-condition assessing server system S generates a driving-time physiological feature, a non-driving-time physiological feature, and a driving-characteristic feature, corresponding to each period (Step S41).

Specifically, the control unit 16 calculates, as the first driving-time physiological feature, differences between each of the period driving-time physiological data on the driving day (for example, the average value and the baseline of the trend of the blood pressure, heart rate, respiratory rate, etc. of the subject T on the driving day) and each of the received driving-time physiological data (current values) using each period driving-time physiological data on the driving day which is an example of the first period or the second period. Incidentally, for each physiological data such as blood pressure, heart rate, respiratory rate, etc., there are respective features belonging to the first driving-time physiological futures.

The control unit 16 calculates, as the second driving-time physiological feature, differences between each period driving-time physiological data in a relatively short period (the average value and the baseline of the trend of the blood pressure, heart rate, respiratory rate, etc. of the subject T in a relatively short period) and each received driving-time physiological data using each period driving-time physiological data in a relatively short period which is an example of the first period or the second period. For each physiological data such as blood pressure, heart rate, respiratory rate, etc., there are respective features belonging to the second driving-time physiological futures.

The control unit 16 calculates slopes of the change over time according to age as the third driving-time physiological feature using each period driving-time physiological data in a relatively long period (for example, one year unit) which is an example of the first period or the second period. For each physiological data such as blood pressure, heart rate, respiratory rate, etc., there are respective features belonging to the second driving-time physiological futures.

The control unit 16 calculates, as the fourth driving-time physiological feature, degrees of difference between the base line of the change over time according to age and each received driving-time physiological data (current value) using each period driving-time physiological data in a relatively long period (for example, one year unit) which is an example of the first period or the second period. For each physiological data such as blood pressure, heart rate, respiratory rate, etc., there are respective features belonging to the fourth driving-time physiological futures.

The control unit 16 calculates, as the first non-driving-time physiological feature, differences between each of the period driving-time physiological data in a relatively short period and statistics of each period non-driving-time physiological data on that day using each period non-driving-time physiological data in a relatively short period which is an example of the first period or the second period.

The control unit 16 calculates slopes of the change over time as the second non-driving-time physiological feature using each period non-driving-time physiological data in a relatively long period (for example, one year unit) which is an example of the first period or the second period.

The control unit 16 calculates, as the third non-driving-time physiological feature, degrees of difference between the base line of the change over time and each period non-driving-time physiological data on that day using each period non-driving-time physiological data in a relatively long period which is an example of the first period or the second period.

The control unit 16 calculates, as the first driving-characteristic feature, differences between each of the period driving-characteristic data on the driving day (the average value and the baseline of the trend of the wandering degree, inter-vehicle distance, etc. of the subject T on the driving day) and each of the received driving-characteristic data (current values) using each driving-characteristic data on the driving day which is an example of the first period or the second period. Incidentally, for each driving-characteristic data such as the wandering degree, inter-vehicle distance, etc., there are respective features belonging to the first driving-characteristic futures.

The control unit 16 calculates, as the second driving-characteristic feature, differences between each of the period driving-characteristic data in the relatively short period (the average value and the baseline of the trend of the wandering degree, inter-vehicle distance, etc. of the subject T in the relatively short period) and each of the received driving-characteristic data using each driving-characteristic data in the relatively short period which is an example of the first period or the second period. For each driving-characteristic data, there are respective features belonging to the second driving-characteristic.

The control unit 16 calculates slopes of the change over time as the third driving-characteristic feature using each period driving-characteristic data in a relatively long period (for example, one year unit) which is an example of the first period or the second period. For each driving-characteristic data, there are respective features belonging to the second driving-characteristic.

The control unit 16 calculates, as the fourth driving-characteristic feature, degrees of difference between the base line of the change over time according to age and each received driving-characteristic data (current value) using each period driving-characteristic data in a relatively long period (for example, one year unit) which is an example of the first period or the second period. For each driving-characteristic data, there are respective features belonging to the fourth driving-characteristic.

The control unit 16 calculates, as the first driving-time/non-driving-time physiological feature, a difference (subtraction, ratio, degree of difference, etc.) between the period non-driving-time period physiological data on the driving day and the current value of the driving-time physiological data. Incidentally, the driving-time/non-driving-time physiological feature may be a difference between the current value of the driving-time physiological data and the period non-driving-time period physiological data in the relatively short period or the relatively long period.

In this manner, the physiological-condition assessing server device 10 functions as an example of the driving-time/non-driving-time physiological feature generating means for generating driving-time/non-driving-time physiological characteristics indicating feature of physiological data of the subject while driving, based on difference between the driving-time physiological data and the period non-driving-time physiological data corresponding to at least one of the first period and the second period.

Incidentally, in case of a season which is an example of the first period or the second period (it is the spring-period if the measured time point of each received driving time physiological data belongs to spring), the difference between each seasonal period driving-time physiological data (the average value and the baseline of the trend of the blood pressure, heart rate, respiratory rate, etc. in the spring-period) and each of the received driving-time physiological data is one of the driving-time physiological features.

In addition, in case of a season which is an example of the first period or the second period (it is the spring-period if the measured time point of each received driving time physiological data belongs to spring), the difference between each seasonal period driving-time physiological data (the average value and the baseline of the trend of the wandering degree, inter-vehicle distance, etc. of the subject T in the spring-period) and each of the received driving-time physiological data is one of the driving-time physiological features.

Incidentally, the control unit 16 may set the age data as one of the features. In addition, the control unit 16 may further subdivide each of the above features as sub features according to age data.

Incidentally, the control unit 16 may set the meteorological data as one of the features.

In addition, the control unit 16 may further subdivide each of the above features as sub features according to meteorological data.

In this manner, the physiological-condition assessing server device 10 functions as an example of the driving-time physiological feature generating means for generating a driving-time physiological feature indicating feature of the physiological data of the subject while driving, from the driving-time physiological data and the period driving-time physiological data. The physiological-condition assessing server device 10 functions as an example of the driving-characteristic feature generating means for generating a driving-characteristic feature indicating feature of the driving characteristic of the subject while driving, from the driving-characteristic data and the period driving-characteristic data. The physiological-condition assessing server device 10 functions as an example of the non-driving-time physiological feature generating means for generating a non-driving-time physiological feature indicating feature of the physiological data of the subject while not driving, from the period non-driving-time physiological data.

In this manner, the physiological-condition assessing server device 10 functions as an example of the driving-time physiological feature generating means for generating a driving-time physiological feature indicating feature of the physiological data of the subject while driving, from the driving-time physiological data and the period driving-time physiological data. The physiological-condition assessing server device 10 functions as an example of the driving-characteristic feature generating means for generating a driving-characteristic feature indicating feature of the driving characteristic of the subject while driving, from the driving-characteristic data and the period driving-characteristic data. The physiological-condition assessing server device 10 functions as an example of the non-driving-time physiological feature generating means for generating a non-driving-time physiological feature indicating feature of the physiological data of the subject while not driving, from the period non-driving-time physiological data.

Next, the physiological-condition assessing server system S normalizes each of the features (Step S42). Specifically, the control unit 16 converts the value of each feature from 0 to a value of 1. For example, the control unit 16 normalizes the data on a linear scale, logarithmic scale, etc., assuming that the maximum values of each physiological data and driving-characteristic data of the subject T in the past, human maximum value, maximum value by gender, etc. are set to 1 (minimum value is 0). In case of meteorological data, the control unit 16 replaces the weather with discrete data (for example, sunny: 0, cloudy: 0.5, rain: 1).

Incidentally, in case of atmospheric pressure, the control unit 16 may normalize the data by setting the maximum value, etc. to 1 (the minimum value is 0), by a linear scale, a logarithmic scale, etc. In addition, on basis of the past average pressure (for example, 1010 hPa), the control unit 16 may be set to 1 when the atmospheric pressure is higher than the average atmospheric pressure, and 0 when the atmospheric pressure is lower than the average atmospheric pressure.

In addition, in a situation where the set value such as the maximum value and the minimum value is out of the set value, the control unit 16 may hold the maximum value (or the minimum value) so far, correct the weight of the feature using the maximum value (or minimum value) so far and the value of new data, and update the maximum value, etc. to hold. Since it is difficult to normalize the data itself, this has the effect of adjusting the weight side to lower the dependency on the scale of the data.

Next, the physiological-condition assessing server system S selects features depending on a physiological condition to assess (Step S43).

For example, in case of determining the risk of cardiovascular disease, the control unit 16 selects the first driving-time physiological feature, the second driving-time physiological feature, the third driving-time physiological feature, the first non-driving-time physiological feature, the second non-driving-time physiological feature, the third non-driving-time physiological feature, the first driving-characteristic feature, the second driving-characteristic feature, the first driving-time/non-driving-time physiological feature, age, and weather.

For example, in case of determining the risk of sleep apnea syndrome, the control unit 16 selects the first driving-time physiological feature, the second driving-time physiological feature, the first non-driving-time physiological feature, the first driving-characteristic feature, the second driving-characteristic feature, the first driving-time/non-driving-time physiological feature, age, and weather.

For example, in case of determining a disease risk (for example, risk of dementia) to be utilized for diagnosis support in a medical institution, etc., the control unit 16 selects the second non-driving-time physiological feature, the third non-driving-time physiological feature, the third driving-characteristic feature, the fourth driving-characteristic feature, and weather.

In this manner, the physiological-condition assessing server device 10 functions as an example of the feature selecting means for selecting a feature used in the physiological condition, for each physiological condition among a plurality of physiological conditions to be assessed, from a plurality of the driving-time physiological features, a plurality of the driving-characteristic features, and a plurality of the non-driving-time physiological features.

Next, the physiological-condition assessing server system S assesses a physiological condition by a classifier (Step S44). Specifically, the control unit 16 inputs the features selected corresponding to the physiological condition to be assessed (for each disease, health condition is good or not, etc.) into the linear classifier (for example, a pattern recognition model of a support vector machine, etc.), and outputs the physiological condition.

The physiological-condition assessing server device 10 assesses the physiological condition by the classifier in the feature space of the feature vectors configured by the selected features.

Herein, examples of the linear classifier include, for example, a function $f(x)=\mathrm{sgn}(\Sigma w_i x_i + b)$ ($i=1 \ldots m$) for the feature $x_i$ (weight $w_i$, constant b). Examples of the a nonlinear classifier include, for example, an $f(x)=\mathrm{sgn}(\Sigma w_i K(x, x_i)+b)$ ($i=1 \ldots m$). Herein, the function $K(x, x_i)$ is a kernel function, for example, a Gaussian function.

The classifier corresponding to the physiological condition to be assessed is prepared. For example, for each disease, the type and number of the feature $x_i$, the value of the weight w, the value of the constant b, the presence or absence of a kernel function, the functional form of the kernel function, etc. are different. In addition, the classifier may be prepared for each threshold of occurrence of a certain illness (first threshold, . . . , nth threshold).

Incidentally, in the parameter correction of the classifier in step S17, the type and number of the feature $x_i$, the value of the weight w, the value of the constant b, the presence/absence of the kernel function, the functional form of the kernel function, etc. are modified. In addition, the parameter of the identifier may be corrected by the gradient method.

The physiological condition may be assessed by applying machine learning such as neural network, genetic algorithm, Bayesian network, decision tree learning, logistic regression etc. to the selected features.

In this manner, the physiological-condition assessing server device 10 functions as an example of the physiological-condition assessing means for assessing a physiological condition of the subject, from the non-driving-time physiological feature and at least one of the driving-time physiological feature and the driving-characteristic feature. The physiological-condition assessing server device 10 functions as an example of the physiological-condition assessing means for assessing the physiological condition of the subject in a feature space of feature vectors composed of the non-driving-time physiological feature and at least one of the driving-time physiological feature and the driving-characteristic feature.

As thus described, according to this embodiment, considering the influence of subject T's biorhythm and external environment for driving-time physiological data and driving-characteristics data in a state where predetermined physical and mental load amount exist while driving the vehicle V in which a change in physiological condition appears easily, each of features (the driving-time physiological feature, the driving-characteristic feature and the non-driving-time physiological feature) quantified to assess the physiological condition are generated from the period driving-time physiological data (acquired from the first storage means that storages the driving-time physiological data measured in the past), the period non-driving-time physiological data (acquired from the second storage means that storages the non-driving-time physiological data measured in the past), and the period driving-characteristic data (acquired from the third storage means that storages the driving-characteristic data measured in the past) corresponding to a plurality of periods such as the first period and the second period having a different length to the first period. Accordingly, since the various features from the physiological data, the driving-characteristic data different from the physiological data, and data due to the difference in the load on the subject T such as when driving or when non-driving (for example, measurement time at the home H and measurement time in the medical institution) are used, it is possible to evaluate or analyze the physiological conditions more accurately and quantitatively. Furthermore, it is possible to capture signs of changes in various physiological conditions.

In addition, since the difference in load applied to the subject T such as driving or non-driving is discriminated and compared, it is possible to assess the physiological conditions with higher accuracy.

In addition, by capturing signs of changes in physiological conditions as soon as possible, it is possible to conduct notification to encourage consultation before sickness progresses, and to conduct notification before changing rapidly during driving.

It is possible to determine by discerning the physiological condition of the subject T by a linear or nonlinear classifier in the feature space of the feature vectors, in case of assessing the physiological condition of the subject T in the feature space of the feature vectors composed of the non-driving-time physiological feature and at least one of the driving-time physiological feature and the driving-characteristic feature. In addition, it is possible to cope with various disease/symptom developing risks by changing the time axis of past data and changing parameters of the classifier used for determination.

It is possible to capture signs of changes in physiological conditions by capturing values overflowing clusters (region define by the classifier) in the feature space.

In addition, in case of nonlinear classifier, it is possible to distinguish easily between the clusters, even when the boundaries of each cluster in the feature space are intricately entered into each other.

In addition, in case that the result of assessing the physiological condition is incorrect, the more the data is collected, the better it learns, and the accuracy of the assessing the physiological condition improves by modifying the parameters of the classifier.

It is possible to assess the physiological conditions accurately for each physiological condition such as the type of disease, in case of selecting a feature used in the physiological condition, for each physiological condition among a plurality of physiological conditions to be assessed, from a plurality of the driving-time physiological features, a plurality of the driving-characteristic features, and a plurality of the non-driving-time physiological features.

For example, in assessing of dementia or cognitive decline, feature concerning the long term past data (relatively long term data) may be used (at this time, feature concerning the short term past data may not be used, or the weight may be lowered). Furthermore, in assessing of dementia or cognitive decline, feature concerning the driving-characteristic data and non-driving-time physiological data (health diagnosis, etc.) may be used (at this time, feature concerning the driving-time physiological data may not be used, or the weight may be lowered).

For example, features concerning both long term past data and short term past data may be used in the developing risk assessment of cardiovascular disease while driving.

For example, features concerning the short-term past data may be used in the developing risk assessment of sleep apnea syndrome while driving (at this time, features concerning the long-term past data may not be used, or the weight may be lowered).

Incidentally, in the cardiovascular disease and the sleep apnea syndrome, features concerning driving-time physiological data that were not used in dementia or of which weights were low are also used.

In addition, since the viewpoint of the time axis can be changed by selecting long term or short term (an example of selection of the first period or the second period) in the selection of feature, it is possible to accurately assess the physiological conditions by the time axis adapted for each physiological condition such as the type of disease.

In addition, the physiological-condition assessing system S generates amount of change over time of the driving-time physiological data as the driving-time physiological feature, from the driving-time physiological data with reference to the first storage means such as the driving-time physiological DB $12b$, based on age of the subject calculated from subject information including birth time of the subject T, generates amount of change over time of the driving-characteristic data as the driving-characteristic feature, with reference to the second storage means such as the driving-characteristic DB $12d$, based on the age of the subject, and generates amount of change over time of the non-driving-time physiological data as the non-driving-time physiological feature, from the non-driving-time physiological data with reference to the third storage means such as the non-driving-time physiological DB $12c$, based on the age of the subject.

In this case, it is possible to evaluate or analyze the physiological conditions accurately and quantitatively, and to assess the physiological conditions accurately, from the features of the trend in the physiological conditions capturing changes over time of the driving-time physiological data and the driving-characteristic data. In addition, it is possible to assess the physiological conditions more accurately by adding an element of the age. For example, even when the slope of the time series change curve (change over time) of the past data or the degree of divergence between the baseline of the change over time and the current value are the same for young people and aged people, it is generally said that the aged people have a higher risk of developing than the young people in cardiovascular diseases such as stroke.

In case that the amount of change over time is the slope of the change over time, it is possible to evaluate or analyze the physiological conditions accurately and quantitatively, and to assess the physiological conditions accurately, from the features capturing changes in physiological conditions trends.

In case that the amount of change over time is the degree of difference from a baseline of the change over time, it is possible to evaluate or analyze the physiological conditions accurately and quantitatively, and to assess the physiological conditions accurately, from the features capturing abnormal values deviating from the baseline.

In case that the amount of change over time is the slope of the change over time and the degree of difference from a baseline of the change over time, since it can be discerned by combining the feature of the slope of the change over time and the feature of the degree of difference, it is possible to evaluate or analyze the physiological conditions accurately and quantitatively, and to assess the physiological conditions accurately. For example, discernment may be improved by the slope of change and the degree of difference, because even with the same degree of divergence, the risk which is an example of quantitative evaluation may be different between slow change and rapid change, in addition, even in the same way of change, the risk may be different even if the degree of difference is different.

In case of generating a driving-time/non-driving-time physiological feature indicating feature of the physiological data of the subject T while driving, based on difference between the driving-time physiological date and the period non-driving-time physiological data corresponding to at least one of the first period and the second period, it is possible to assess the physiological conditions more accurately from the feature of the difference between the physiological data at driving time and at non-driving time.

In case that the first period or the second period is a season, because of comparing the period physiological data considering the biorhythm such as in spring, summer, autumn and winter (the other is morning, noon, night, etc.), the influence of biorhythm is reduced and it is possible to assess the physiological condition more accurately. In addition, accuracy can be improved by collecting and comparing homogeneous data such as the period is morning and the second period is spring, or the first period is morning and the second period is summer, etc.

In case that the first period or the second period is a driving day including the measurement time point of the driving-time physiological data or the measurement time point of the driving-characteristic data, because of including the change in physiological condition (for example, sudden change in physical condition) in one of the features, it is possible to assess the physiological condition more accurately.

Modified Example

The following describes modified examples.

The physiological-condition assessing server device 10 may assess the physiological condition of the subject T according to the meteorological state of the meteorological data acquired in step S22.

For example, the physiological-condition assessing server device 10 generates classified features corresponding to meteorological state based on additional information of meteorological state, further by subdividing each of feature as sub features corresponding to meteorological state. The physiological-condition assessing server device 10 assesses the physiological condition of the subject T by the classifier in the feature space classified corresponding to the meteorological state.

It is possible to accurately assess the physiological condition of the subject T by incorporating physiological influences (for example, blood pressure) of high pressure (sunny) and low pressure (rain), and categorizing physiological data.

In addition, the state of the road surface changes due to meteorological state such as rain, snow, freezing, etc., the field of vision changes during driving, and the driving-characteristic data is directly affected. Depending on the meteorological states, the driving-time physiological data are affected by stress conditions through difficulties in driving due to changes in the state of the road surface, good/bad visibility during driving, etc. Features related to the driving-time physiological data and the driving-characteristic data are categorized, and the physiological condition of the subject T can be assessed with high accuracy.

The physiological-condition assessing server device 10 may form a new feature space (setting a vector of another dimension) in which the meteorological state is added as a feature, and may assess the physiological condition of the subject T with the identifier. The feature of meteorological state may be weather (for example, sunny: 0, cloudy: 0.5, rain: 1), may be different from other meteorological data such as atmospheric pressure, or may be a comprehensive index.

In case of acquiring meteorological data when measuring the driving-time physiological data from the measurement time point of the driving-time physiological data and the position information of the vehicle V when measuring the driving-time physiological data, and of assessing the physiological condition of the subject T according to the meteorological state of the meteorological data, since the meteorological state can be taken into consideration, it is possible to assess the physiological condition with higher accuracy.

The physiological-condition assessing server device 10 may assess the physiological condition of the subject T corresponding to the driving environment information of the vehicle V acquired in step S23.

For example, the physiological-condition assessing server device 10 generates classified features corresponding to information on driving environment based on additional information of information on driving environment, further by subdividing each of feature as sub features according to information on driving environment. The physiological-condition assessing server device 10 assesses the physiological condition of the subject T by the classifier in the feature space classified corresponding to the information on driving environment.

The physiological-condition assessing server device 10 divides the features into sub features based on data classifying the driving-time physiological data and the driving-characteristic data corresponding to whether or not the traffic is congested, whether it is an expressway or not, etc. In addition, physiological-condition assessing server device 10 may categorize the driving-time physiological data and the driving-characteristic data as a comprehensive index, depending on, for example, whether or not the heart rate is likely to rise.

A new feature space may be formed by adding information on driving environment as a feature, and the physiological condition of the subject T may be assess by the identifier. The feature of the information on driving environment may be the degree of congestion, may be different from other information on driving environment, or may be a comprehensive index.

In the case of acquiring the information on driving environment of the vehicle V from the position information of the vehicle V when measuring the driving-time physiological data, and of assessing the physiological condition of the subject T corresponding to the information on driving environment of the vehicle V, since the driving environment such as narrow road, highway, etc. can be known from the position information and it can be inferred what kind of load has been applied to the subject it is possible to assess the physiological condition with higher accuracy.

In addition to the driving-tie physiological data, the physiological-condition assessing server device 10 may acquire medication data on medication of the subject T. For example, the physiological-condition assessing server device 10 acquires the data from the mobile terminal device 20 that accepted input of medication information such as the presence or absence of taking medication and the type of drug. The physiological-condition assessing server device 10 may acquire medication data on medication of the subject T from the medical institution server device 50.

The physiological-condition assessing server device 10 divides the features into sub features based on data classifying the driving-time physiological data, non-driving-time physiological data and the driving-characteristic data corresponding to whether medicine is taken or not. If the measurement is performed within a predetermined time after taking medication, the physiological-condition assessing server device 10 is assumed to be data indicating that the medicine is taken.

Incidentally, the physiological-condition assessing server device 10 may form a new feature space (setting a vector of another dimension) in which the medication condition is added as a feature, and may assess the physiological condition of the subject T with the identifier. For example, in the set dimension, not taking medicine is set to 0, and taking medicine is set to 1.

In addition, even case of taking medication, the physiological-condition assessing server device 10 may evaluate, for example, by multiplying a coefficient corresponding to the time difference in case of not taking medication at a predetermined time.

In the case where medication data on the medication of the subject T is acquired from a terminal device (for example, mobile terminal device 20) that measures the medication data and the physiological condition of the subject T is assessed corresponding to the medication condition of the medication data, it is assessed in consideration of the medication condition. So that it is possible to more accurately quantitatively evaluate or analyze the physiological condition reflecting the medication condition and to accurately assess the physiological condition.

In addition, the physiological-condition assessing server device 10 may use period driving-time physiological data of other subjects, period non-driving-time physiological data of other subjects, period driving-characteristic data of other subjects, etc. In particular, in case that the data is insufficient, the physiological-condition assessing server device 10 uses data of other subjects having the same age, similar gender, and similar constitution to the subject.

In case of acquiring the period driving-time physiological data of another subject corresponding to the first period and the second period, with reference to a fourth storage means for storing the driving-time physiological data of the other subject measured in the past, and generating the driving-time physiological feature, from the driving-time physiological data and the period driving-time physiological data of the other subject, it is possible to complement the data even if the data is insufficient, evaluate or analyze the physiological condition more accurately and quantitatively, and further capture signs of changes in various physiological conditions. In particular, in case of other subjects who are closer in age, same in gender, and similar in constitution to the subject, the accuracy of complementation becomes higher.

In addition, the present invention is not limited to the above embodiments. The above embodiments are merely examples. Any other embodiment that has essentially the same configuration and produces a similar effect as the technical ideas described in the claims of the present invention falls within the scope of the invention.

REFERENCE SIGNS LIST

10: PHYSIOLOGICAL-CONDITION ASSESSING SERVER DEVICE (PHYSIOLOGICAL-CONDITION ASSESSING DEVICE)
12: STORAGE UNIT (STORAGE MEANS)
20: MOBILE TERMINAL DEVICE
30: IN-VEHICLE TERMINAL DEVICE
40: HOME TERMINAL DEVICE
50: MEDICAL INSTITUTION SERVER DEVICE
S: PHYSIOLOGICAL-CONDITION ASSESSING SYSTEM
T: SUBJECT
V: VEHICLE

The invention claimed is:

1. A physiological-condition assessing device comprising:
driving-time physiological data acquiring unit for acquiring a driving-time physiological data of a subject measured when the subject is driving a vehicle, and a measurement time point of the driving-time physiological data;
driving-characteristic data acquiring unit for acquiring a driving-characteristic data indicating a driving characteristic in which the subject drives the vehicle, and a measurement time point of the driving-characteristic data;
period driving-time physiological data acquiring unit for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage unit for storing the driving-time physiological data measured in the past;
period driving-characteristic data acquiring unit for acquiring a period driving-characteristic data corresponding to the first period and the second period, with reference to a second storage unit for storing the driving-characteristic data measured in the past;
period non-driving-time physiological data acquiring unit for acquiring a period non-driving-time physiological data corresponding to at least one of the first period and the second period, with reference to a third storage unit for storing a non-driving-time physiological data measured in the past that is the physiological data of the subject when the subject is not driving the vehicle;
driving-time physiological feature generating unit for generating a driving-time physiological feature indicating feature of the physiological data of the subject while driving, from the driving-time physiological data and the period driving-time physiological data;
driving-characteristic feature generating unit for generating a driving-characteristic feature indicating feature of the driving characteristic of the subject while driving, from the driving-characteristic data and the period driving-characteristic data;

non-driving-time physiological feature generating unit for generating a non-driving-time physiological feature indicating feature of the physiological data of the subject while not driving, from the period non-driving-time physiological data; and physiological-condition assessing unit for assessing a physiological condition of the subject, from the non-driving-time physiological feature and at least one of the driving-time physiological feature and the driving-characteristic feature.

2. The physiological-condition assessing device according to claim 1, wherein
the physiological-condition assessing unit assesses the physiological condition of the subject in a feature space of feature vectors composed of the non-driving-time physiological feature and at least one of the driving-time physiological feature and the driving-characteristic feature.

3. The physiological-condition assessing device according to claim 1, further comprising
feature selecting unit for selecting a feature used in the physiological condition, for each physiological condition among a plurality of physiological conditions to be assessed, from a plurality of the driving-time physiological features, a plurality of the driving-characteristic features, and a plurality of the non-driving-time physiological features.

4. The physiological-condition assessing device according to claim 1, wherein
the driving-time physiological feature generating unit generates amount of change over time of the driving-time physiological data as the driving-time physiological feature, from the driving-time physiological data with reference to the first storage unit, based on age of the subject calculated from subject information including birth time of the subject,
the driving-characteristic feature generating unit generates amount of change over time of the driving-characteristic data as the driving-characteristic feature, with reference to the second storage unit, based on the age of the subject, and
the non-driving-time physiological feature generating unit generates amount of change over time of the non-driving-time physiological data as the non-driving-time physiological feature, from the non-driving-time physiological data with reference to the third storage unit, based on the age of the subject.

5. The physiological-condition assessing device according to claim 4, wherein
the amount of change over time is at least one of a slope of the change over time and a degree of difference from a baseline of the change over time.

6. The physiological-condition assessing device according to claim 1, further comprising
driving-time/non-driving-time physiological feature generating unit for generating a driving-time/non-driving-time physiological feature indicating feature of the physiological data of the subject while driving, based on difference between the driving-time physiological date and the period non-driving-time physiological data corresponding to at least one of the first period and the second period.

7. The physiological-condition assessing device according to claim 1, wherein
the first period or the second period is a season.

8. The physiological-condition assessing device according to claim 1, wherein
the first period or the second period is a driving day including the measurement time point of the driving-time physiological data or the measurement time point of the driving-characteristic data.

9. The physiological-condition assessing device according to claim 1, further comprising
medication-physiological data acquiring unit for acquiring a medication data on medication of the subject, from a terminal device which measures the medication data, wherein
the physiological-condition assessing unit assesses the physiological condition of the subject, depending on a medication condition of the medication data.

10. The physiological-condition assessing device according to claim 1, further comprising
driving-environment information acquiring unit for acquiring driving-environment information of the vehicle, from position information of the vehicle when measuring the driving-time physiological data, wherein
the physiological-condition assessing unit assesses the physiological condition of the subject, depending on the driving-environment information of the vehicle.

11. The physiological-condition assessing device according to claim 1, further comprising
meteorological data acquiring unit for acquiring a meteorological data when measuring the driving-time physiological data, from the measurement time point of the driving-time physiological data and position information of the vehicle when measuring the driving-time physiological data, wherein
the physiological-condition assessing unit assesses the physiological condition of the subject, depending on a meteorological state of the meteorological data.

12. The physiological-condition assessing device according to any claim 1, wherein
the period driving-time physiological data acquiring unit that acquires the period driving-time physiological data of another subject corresponding to the first period and the second period, with reference to a fourth storage unit for storing the driving-time physiological data of the other subject measured in the past, and
the driving-time physiological feature generating unit generates the driving-time physiological feature, from the driving-time physiological data and the period driving-time physiological data of the other subject.

13. A physiological-condition assessing method comprising:
a step in which driving-time physiological data acquiring unit stores acquires a driving-time physiological data of a subject measured when the subject is driving a vehicle, and a measurement time point of the driving-time physiological data;
a step in which driving-characteristic data acquiring unit acquires a driving-characteristic data indicating a driving characteristic in which the subject drives the vehicle, and a measurement time point of the driving-characteristic data;
a step in which period driving-time physiological data acquiring unit acquires a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage unit for storing the driving-time physiological data measured in the past;

a step in which period driving-characteristic data acquiring unit acquires a period driving-characteristic data corresponding to the first period and the second period, with reference to a second storage unit for storing the driving-characteristic data measured in the past;

a step in which period non-driving-time physiological data acquiring unit acquires a period non-driving-time physiological data corresponding to at least one of the first period and the second period, with reference to a third storage unit for storing a non-driving-time physiological data measured in the past that is the physiological data of the subject when the subject is not driving the vehicle;

a step in which driving-time physiological feature generating unit generates a driving-time physiological feature indicating feature of the physiological data of the subject while driving, from the driving-time physiological data and the period driving-time physiological data;

a step in which driving-characteristic feature generating unit generates a driving-characteristic feature indicating feature of the driving characteristic of the subject while driving, from the driving-characteristic data and the period driving-characteristic data;

a step in which non-driving-time physiological feature generating unit generates a non-driving-time physiological feature indicating feature of the physiological data of the subject while not driving, from the period non-driving-time physiological data; and a step in which physiological-condition assessing unit assesses a physiological condition of the subject, from the non-driving-time physiological feature and at least one of the driving-time physiological feature and the driving-characteristic feature.

14. A non-transitory computer-readable storage medium recording a program for a physiological-condition assessing device, for causing a computer to function as:

driving-time physiological data acquiring unit for acquiring a driving-time physiological data of a subject measured when the subject is driving a vehicle, and a measurement time point of the driving-time physiological data;

driving-characteristic data acquiring unit for acquiring a driving-characteristic data indicating a driving characteristic in which the subject drives the vehicle, and a measurement time point of the driving-characteristic data;

period driving-time physiological data acquiring unit for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage unit for storing the driving-time physiological data measured in the past;

period driving-characteristic data acquiring unit for acquiring a period driving-characteristic data corresponding to the first period and the second period, with reference to a second storage unit for storing the driving-characteristic data measured in the past;

period non-driving-time physiological data acquiring unit for acquiring a period non-driving-time physiological data corresponding to at least one of the first period and the second period, with reference to a third storage unit for storing a non-driving-time physiological data measured in the past that is the physiological data of the subject when the subject is not driving the vehicle;

driving-time physiological feature generating unit for generating a driving-time physiological feature indicating feature of the physiological data of the subject while driving, from the driving-time physiological data and the period driving-time physiological data;

driving-characteristic feature generating unit for generating a driving-characteristic feature indicating feature of the driving characteristic of the subject while driving, from the driving-characteristic data and the period driving-characteristic data;

non-driving-time physiological feature generating unit for generating a non-driving-time physiological feature indicating feature of the physiological data of the subject while not driving, from the period non-driving-time physiological data; and physiological-condition assessing unit for assessing a physiological condition of the subject, from the non-driving-time physiological feature and at least one of the driving-time physiological feature and the driving-characteristic feature.

15. A physiological-condition assessing system comprising: a physiological-condition assessing device for assessing a physiological condition of a subject; a mobile terminal device carried by the subject; and an in-vehicle terminal device installed in a vehicle that the subject drives, wherein the physiological-condition assessing device comprises:

driving-time physiological data acquiring unit for acquiring a driving-time physiological data of the subject measured when the subject is driving the vehicle, and a measurement time point of the driving-time physiological data;

driving-characteristic data acquiring unit for acquiring a driving-characteristic data indicating a driving characteristic in which the subject drives the vehicle, and a measurement time point of the driving-characteristic data;

period driving-time physiological data acquiring unit for acquiring a period driving-time physiological data corresponding to a first period including the measurement time point of the driving-time physiological data and the measurement time point of the driving-characteristic data, and to a second period having a different length to the first period and including the measurement time point of the driving-time physiological data and the measurement time point of the driving-characteristic data, with reference to a first storage unit for storing the driving-time physiological data measured in the past;

period driving-characteristic data acquiring unit for acquiring a period driving-characteristic data corresponding to the first period and the second period, with reference to a second storage unit for storing the driving-characteristic data measured in the past;

period non-driving-time physiological data acquiring unit for acquiring a period non-driving-time physiological data corresponding to at least one of the first period and the second period, with reference to a third storage unit for storing a non-driving-time physiological data measured in the past that is the physiological data of the subject when the subject is not driving the vehicle;

driving-time physiological feature generating unit for generating a driving-time physiological feature indicating feature of the physiological data of the subject while driving, from the driving-time physiological data and the period driving-time physiological data;

driving-characteristic feature generating unit for generating a driving-characteristic feature indicating feature of the driving characteristic of the subject while driving, from the driving-characteristic data and the period driving-characteristic data;

non-driving-time physiological feature generating unit for generating a non-driving-time physiological feature indicating feature of the physiological data of the subject while not driving, from the period non-driving-time physiological data; and physiological-condition assessing unit for assessing the physiological condition of the subject, from the non-driving-time physiological feature and at least one of the driving-time physiological feature and the driving-characteristic feature.

* * * * *